United States Patent [19]

Iwata et al.

[11] Patent Number: 5,262,319

[45] Date of Patent: Nov. 16, 1993

[54] METHOD FOR OBTAINING BONE MARROW FREE OF TUMOR CELLS USING TRANSFORMING GROWTH FACTOR β3

[75] Inventors: Kenneth K. Iwata, Westbury; J. Gordon Foulkes, Huntington; Peter T. Dijke, Port Washington; John D. Haley, Great Neck, all of N.Y.

[73] Assignee: Oncogene Science, Inc., Uniondale, N.Y.

[21] Appl. No.: 543,341

[22] Filed: Jun. 25, 1990

Related U.S. Application Data

[63] Continuation-in-part of Ser. No. 353,410, May 17, 1989, abandoned, which is a continuation-in-part of Ser. No. 183,824, Apr. 20, 1988, abandoned, which is a continuation-in-part of Ser. No. 111,022, Oct. 20, 1987, which is a continuation-in-part of Ser. No. 922,121, Oct. 20, 1986, abandoned, which is a continuation-in-part of Ser. No. 847,931, Apr. 7, 1986, abandoned, which is a continuation-in-part of Ser. No. 725,003, Apr. 19, 1985, abandoned.

[51] Int. Cl.$^5$ .................. C12N 5/08; C07K 15/14
[52] U.S. Cl. .................. 435/240.2; 435/240.25; 530/399
[58] Field of Search .......... 435/240.2, 240.21, 240.25; 514/2, 8, 25; 530/395, 399

[56] References Cited

PUBLICATIONS

Roberts et al., "Type B Transforming Growth Factor: A Bifunctional Regulator of Cellular Growth," *Proc. Natl. Acad. Sci. USA* 82:119–123, Jan. 1985.

Lemoli et al., "TGF-beta 3 Protects Normal Human Hematopoietic Progenitor Cells Treated with 4-Hydroxyperoxycyclophosphamide in vitro," *Exp. Hematol.* 20(11):1252–1256, 1992.

*Primary Examiner*—David L. Lacey
*Assistant Examiner*—Robert D. Budens
*Attorney, Agent, or Firm*—John P. White

[57] ABSTRACT

The present invention provides (1) an antibody which (a) specifically binds to human TGF-β3 and (b) exhibits substantially no cross reactivity with TGF-β1 or TGF-β2 and (2) antibodies directed against the pro region of the TGF-β precursor. Further, this invention provides a pharmaceutical composition comprising the pro region of the TGF-β precursor. Also, this invention provides methods for diagnosing, detecting and treating subjects suffering from disorders associated with TGF-β3.

1 Claim, 23 Drawing Sheets

```
  N  C  C  V  R  P  L  Y  I  D  F  R  Q  D  L  G  W  K  W  V  H  E  P  K  G  Y  Y  A  N  F  C  S  G
GAACTGCTGTGTGCGCCCCCTCTACATTGACTTCCGACAGGATCTGGGCTGGAAGTGGGTCCATGAGCCTAAGGGCTACTATGCCAACTTCTGCTCAGGC
     1210      1220      1230      1240      1250      1260      1270      1280      1290      1300
  P  C  P  Y  L  R  S  A  D  T  T  H  S  T  V  L  G  L  Y  N  T  L  N  P  E  A  S  P  C  C  V
CCTTGCCCATACCTCCGCAGTGCAGACACAACCCACAGCACGGTGCTGGGACTGTACAACACTCTGAACCCTGAAGCATCTCCGCCTTGCTGCGTGC
     1310      1320      1330      1340      1350      1360      1370      1380      1390      1400
  P  Q  D  L  E  P  L  T  I  L  Y  Y  V  G  R  T  P  K  V  E  Q  L  S  N  M  V  K  S  C  K  C  S
CCCAGGACCTGGAGCCCCTGACCATCCTGTACTATGTTGGGAGGACCCCCAAAGTGGAGCAGCTCTCCAACATGGTGAAGTCTTGTAAATGTAGCTG
     1410      1420      1430      1440      1450      1460      1470      1480      1490      1500
AGACCCCACGTGCGACGTGCCTGACTGCCGCCTCTCGGGAACAACAAGCAACACACAACCTCACTGAGAGGCCTG
     1510      1520      1530      1540      1550      1560      1570      1580      1590      1600
GAGCCCACAACCTTCGGCTCCGGGCAAATGGCTGAGATGGAGGTTTCCTTTTGGAACATTCTTTCTTGCTCCTGAGAATCACGGTGGTAAAGAAAG
     1610      1620      1630      1640      1650      1660      1670      1680      1690      1700
                                            Hga I↓
TGTGGGTTTGGTTAGAGGAAGGCTGAACTCTTCAGAACACACAGACTTTCTGTGACGCAGAGAGGGATGGGATAGGAGAAAGGGATGGTAAGTTGA
     1710      1720      1730      1740      1750      1760      1770      1780      1790      1800
GATGTGTGTGGCAATGGGGGATTTGGGCTACCCTAAAGGGGAAGGAAGGCAGAATGGCTCAGGGAAGACTGGAAGACACTTCAGATCTGAGG
     1810      1820      1830      1840      1850      1860      1870      1880      1890      1900
TTGGATTTGCTCATTGCTGTGTACCACATCTGCTCTAGGAATCTGGATTATGTTATACAAGGCAAGCATTTTTTTTTTAAAGACAGGTTACGAAGA
     1910      1920      1930      1940      1950      1960      1970      1980      1990      2000
CAAAGTCCCAGAATGTATCTCATACTGTCTGGGATTAAGGCAAATCTATTACTTTTGCAAACTGTCCTCTACATCAATTAACATCGTGGGTCACTACA
     2010      2020      2030      2040      2050      2060      2070      2080      2090      2100
GGGAGAAAATCCAGGTCATGCAGTTCCTGGCCATCAACTGTATTGGGCCTTTTGGATATGCTGAACGCAGAAGAAGGGTGAAATCAACCCTCTCCTG
     2110      2120      2130      2140      2150      2160      2170      2180      2190      2200
TCTGCCTCTGGGTCCCCTCTCCACCTTCTCCCTGATCATCATATTTCCCCTTGGTTAGACACTTGGTTGGAAGACGCTTCAGGATGCACATTTCTGGATTGT
     2210      2220      2230      2240      2250      2260      2270      2280      2290      2300
GGTTCCATGCAGGGTTGGGGCATTATGGGTTCTTCCCCCACTTCGTGTTCATTGGTGTTCCTGGAAGCAGGTGCGACAACATGTG
     2310      2320      2330      2340      2350      2360      2370      2380      2390      2400
AGGCATTCGGGGAAGCTCGACAGTGCCACACAGTGACTTGGCCCCAGACGCATAGACTGAGGTATAAAGACAAGTATGAATATTACTCTCAAAATCTTT
     2410      2420      2430      2440      2450      2460      2470      2480      2490      2500
GTATAAATAAATATTTTTGGGCATCCTG poly(A)
     2510      2520
```

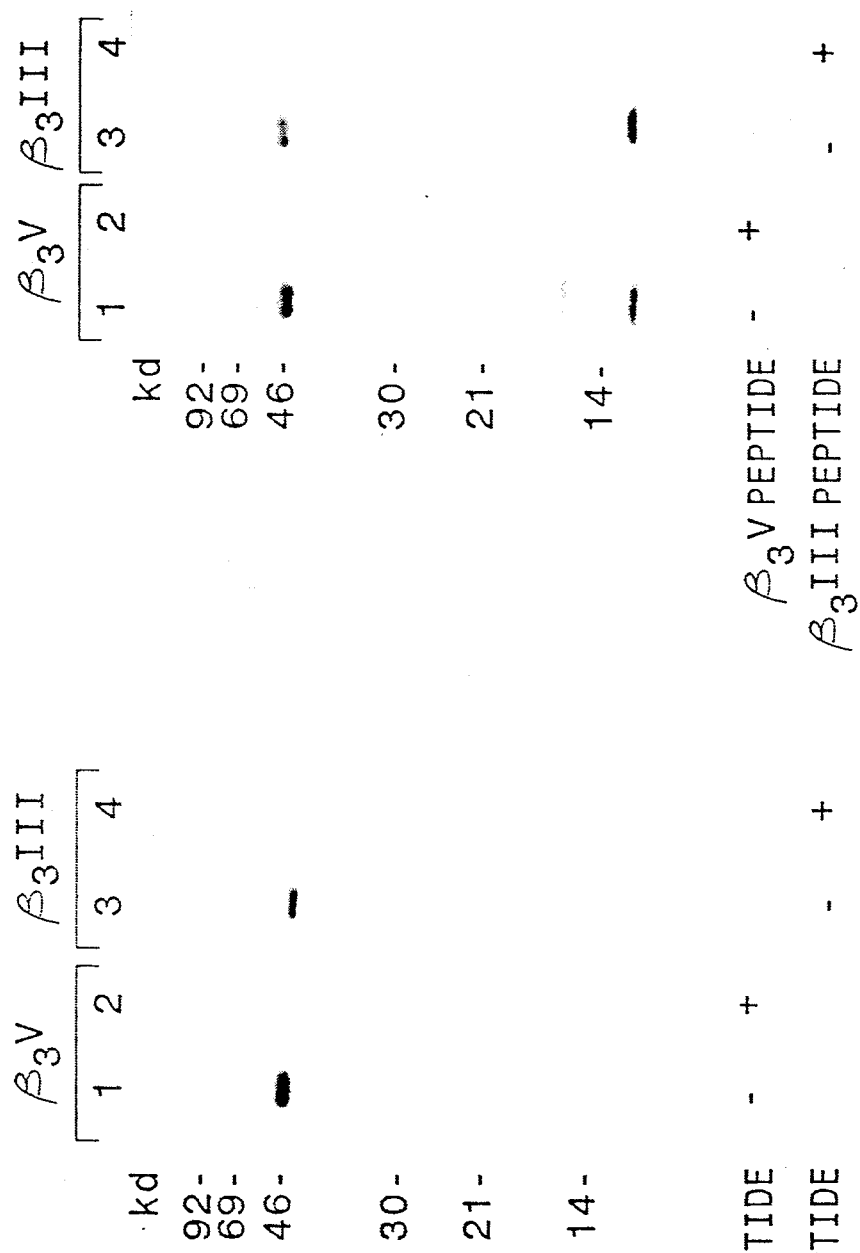

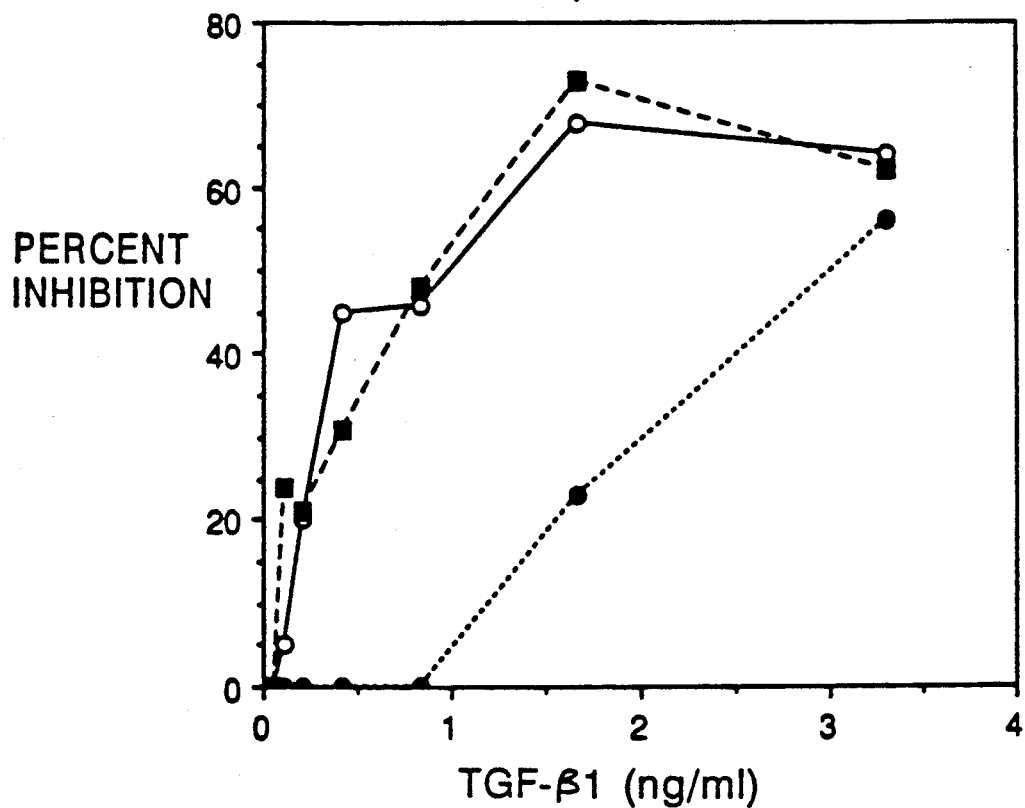

TGF-β3 CHEMOPROTECTION OF MINK CELLS FROM COLCHICINE

TGF-β3 CHEMOPROTECTION OF MINK CELLS FROM VINBLASTINE

METHOD FOR OBTAINING BONE MARROW FREE OF TUMOR CELLS USING TRANSFORMING GROWTH FACTOR β3

This application is a continuation-in-part of U.S. Ser. No. 353,410, filed May 17, 1989, now abandoned, which is a continuation-in-part of U.S. Ser. No. 183,824, filed Apr. 20, 1988, now abandoned, which is a continuation-in-part of U.S. Ser. No. 111,022, filed Oct. 20, 1987 now abandoned, which is a continuation-in-part of U.S. Ser. No. 922,121, filed Oct. 20, 1986, now abandoned, which was a continuation-in-part of U.S. Ser. No. 847,931, filed Apr. 7, 1986, now abandoned, which was a continuation-in-part of U.S. Ser. No. 725,003, filed Apr. 19, 1985, now abandoned, the contents of each are hereby incorporated by reference into the present application.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

Transforming growth factor β (TGF-β) is part of a family of multifunctional proteins which appear to modulate, alone or in combination with other molecules, cell proliferation and differentiation. Reportedly, TGF-β, which comprises a mature a precursor and a pro region of the precursor form, contains a subclass of molecules designated TGF-β1, -β2, -β3, -β4, and -β5 (24, 25, 26).

Mature TGF-β has been isolated from various species. Murine, bovine, human, and porcine TGF-β have been isolated and show very little difference in amino acid composition (26, 27, 28, 29).

The cDNA sequence of mature TGF-β, its expression in both normal and transformed cells, and methods of producing biologically active mature TGF-β in eucaryotic cells have been described (26, 28, 29, 54, 55).

Antibodies directed to mature TGF-β1 and -β2 have previously been described (32, 33, 34, 35, 36). Because of the high homology between the various isoforms of mature TGF-β, these antibodies exhibit substantial cross reactivity. Antibodies which are specifically directed to human mature TGF-β3 and exhibit no substantial cross reactivity with other TGF-β3 isoforms have not been described.

SUMMARY OF THE INVENTION

The present invention provides (1) an antibody which (a) specifically binds to human TGF-β3 and (b) exhibits substantially no cross reactivity with TGF-β1 or TGF-β2 and (2) antibodies directed against the pro region of the TGF-β precursor. Further, this invention provides a pharmaceutical composition comprising the pro region of the TGF-β precursor. Also, this invention provides methods for diagnosing, detecting and treating subjects suffering from disorders associated with a TGF-β.

(B) shows the dose response of mink cell growth inhibition using acid activation serum free supernatants CHO 6.35/20 nM transfectant and CHO 6.35 transfectant. Cell growth was quantitated by the metabolism of MTT.

Figure 6:
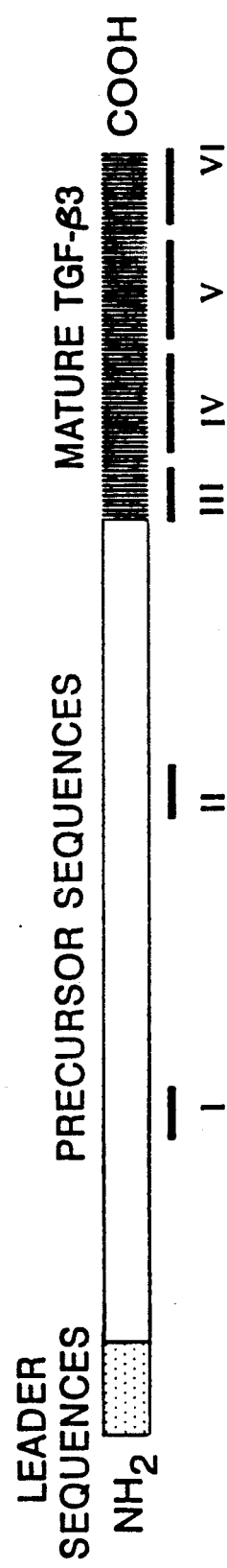

FIG. 6 shows the relative location of the various TGF-β3 peptides used as antigens.

Figure 7:
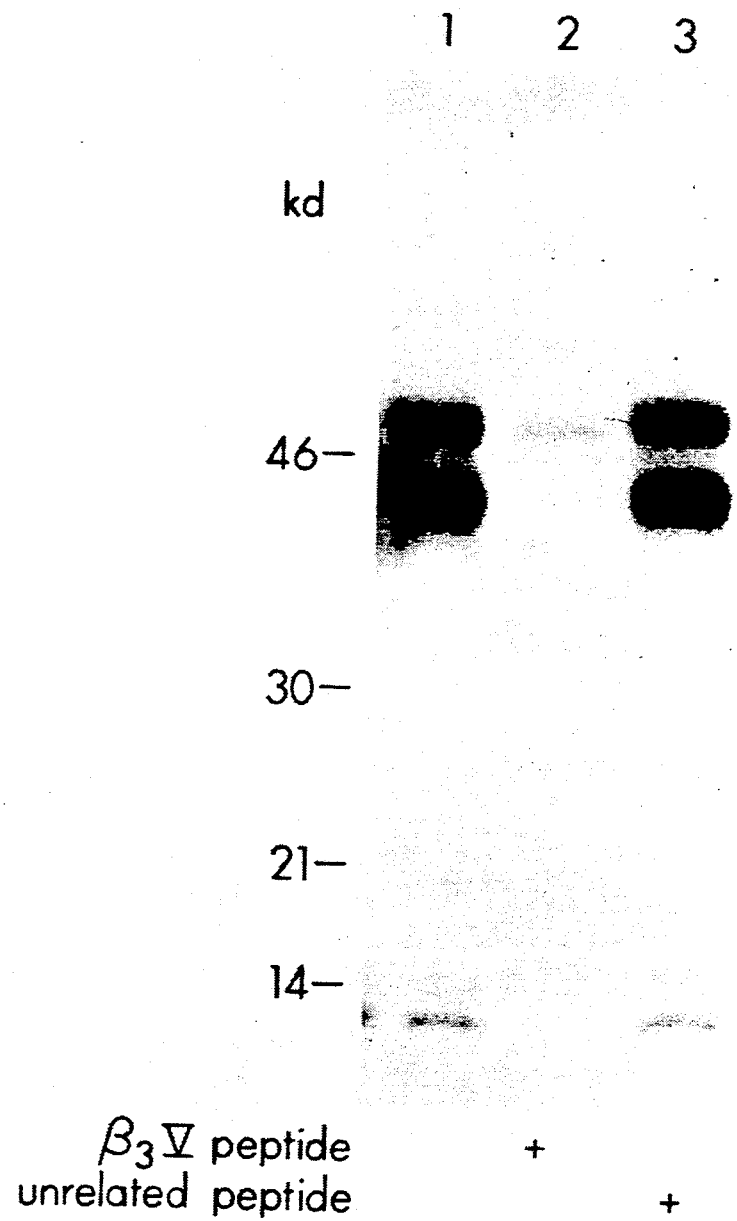

FIG. 7 shows the immunoprecipitation of native recombinant TGF-β3 protein by β3V antibody.

Figure 8B:
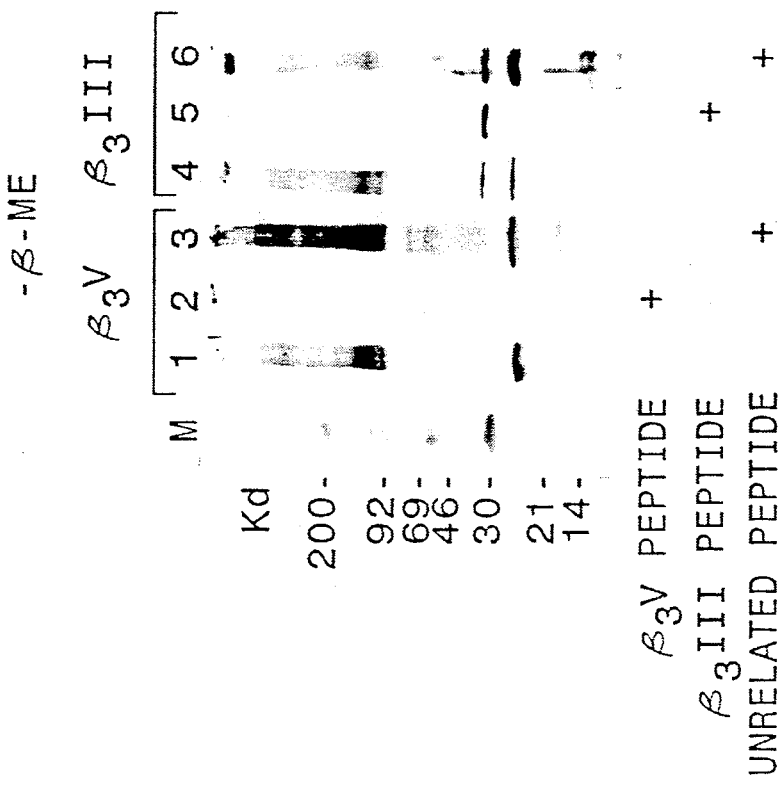
Figure 8A:
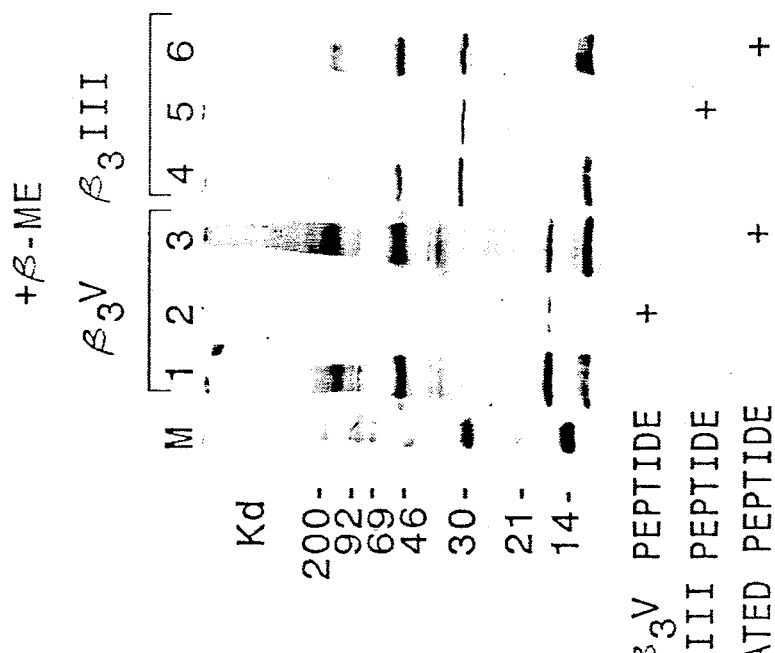
Figure 10A:
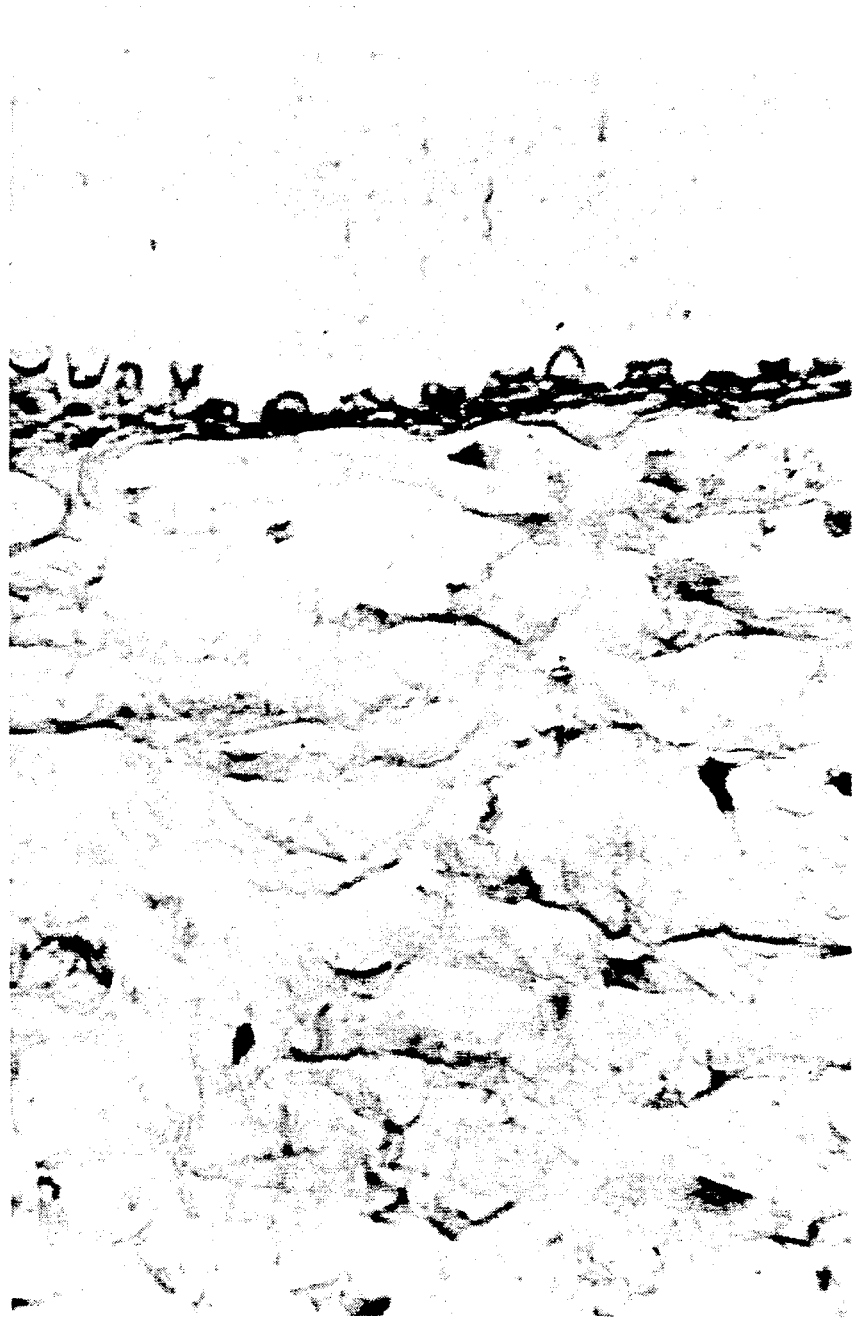
Figure 10B:
Figure 10C:
Figure 10D:
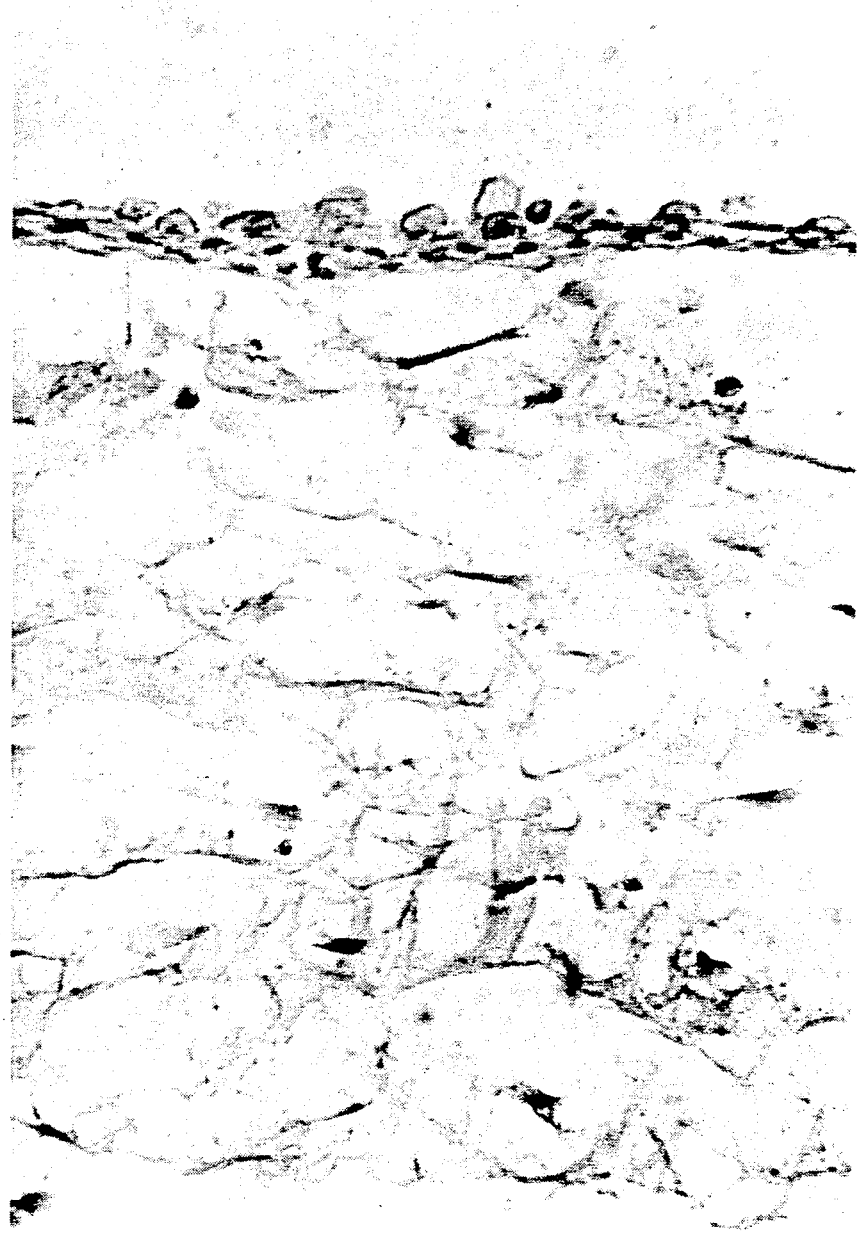

FIGS. 8A and 8B (A) shows the immunoblot of TGF-β3 from conditioned media of CHO 6.35/20 nM transfectant using β3III and β3V antibodies for detection from gels under reducing conditions.

(B) shows the immunoblot of TGF-β3 from conditioned media of CHO 6.35/20 nM transfectant using β3III and β3V antibodies for detection from gels under non-reducing conditions.

FIGS. 9A and 9B show a Western blot of cell extract (9A) and conditioned media (9B) of the CHO 6.35/20 nM transfectant using β3V antibody for detection.

FIGS. 10A, 10B, 10C and 10D show the staining to paraffin sections of human umbilical cord by β3V antibody and control antibody. A and C show fibroblast and epithelial staining and smooth muscle fiber staining, respectively, by β3V antibody. B and D show no staining by control rabbit polyclonal antibody.

Figure 11A:
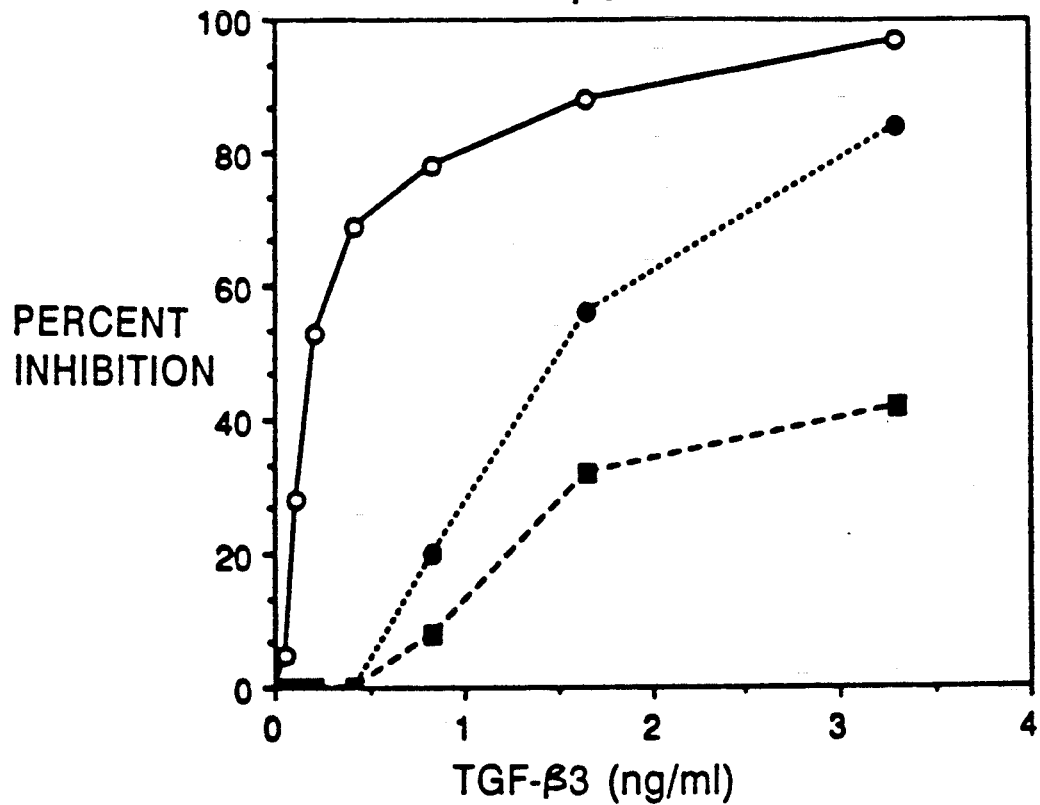
Figure 11C:
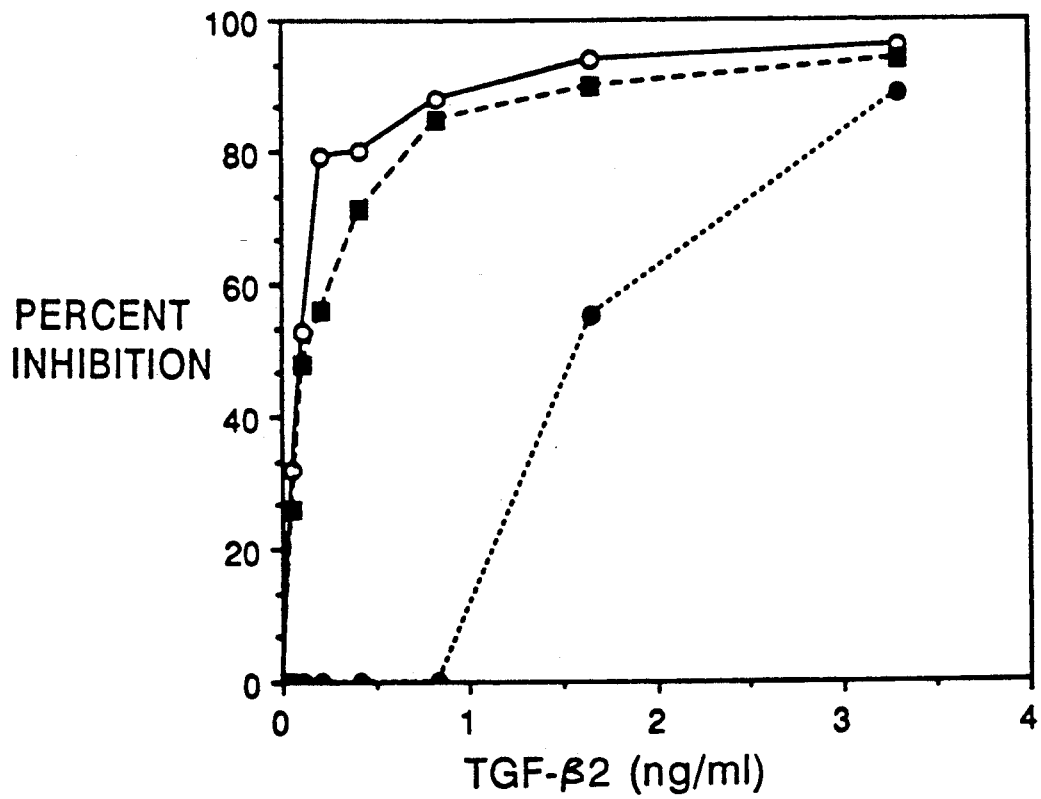

FIGS. 11A, 11B and 11C show specific neutralization of TGF-β3 inhibition of mink cell growth by the antibody β3V.

Figure 12A:
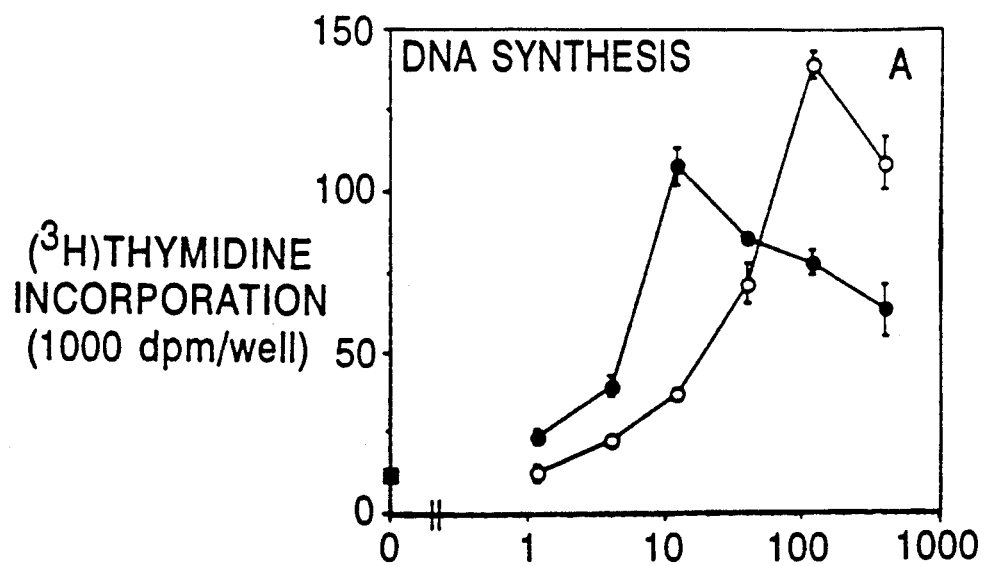
Figure 12B:
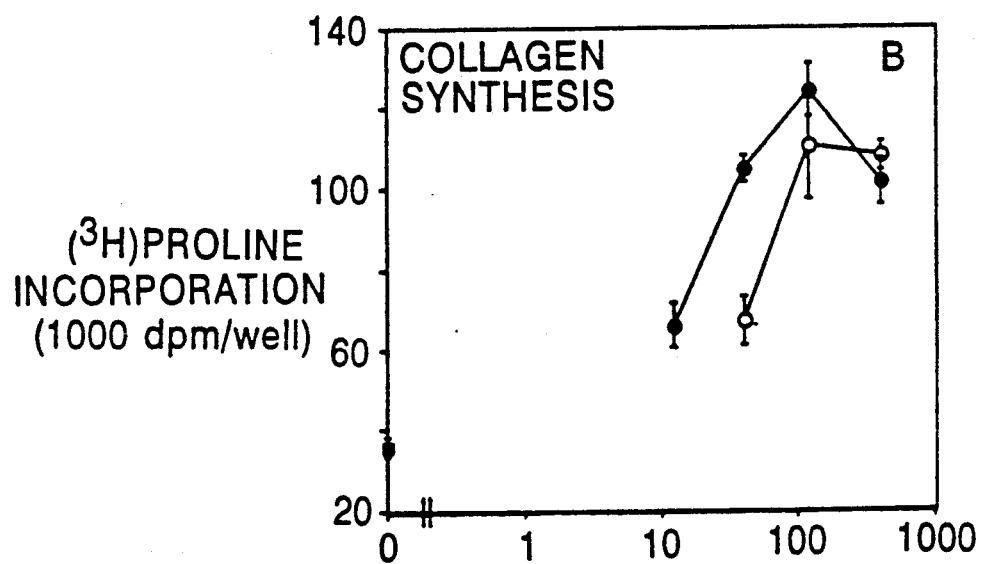
Figure 12C:
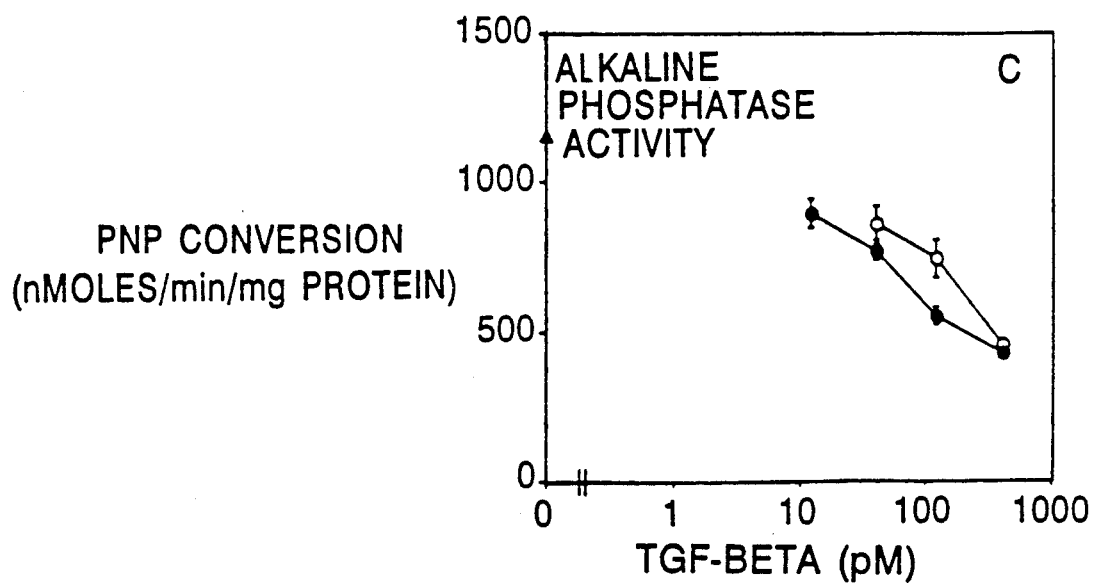

FIGS. 12A, 12B and 12C. Effect of TGF-β3 (closed circles) and TGF-β1 (open circles) on DNA synthesis, collagen synthesis and alkaline phosphatase activity. Osteoblast-enriched cultures from fetal rat parietal bone were cultured to confluence and then serum deprived for 20 hours prior to a 23 hours treatment with either TGF-β3 or TGF-β1 at the concentrations shown. (A) DNA synthesis rates were measured by labelling cells with [$^3$H]thymidine for the last 2 hours of culture; acid-insoluble material was assayed by scintillation counting.

(B) Collagen synthesis was measure by labeling with [$^3$H]proline the last 2 hours of culture; acid-insoluble cell extracts were digested with nonspecific protease-free bacterial collagenase and radioactivity was determined in the enzyme-released supernatants.

(C) Alkaline phosphatase activity was measured in cell extracts by hydrolysis of p-nitrophenyl phosphate to p-nitrophenol (PNP). Data are the means ±SEM of four to six replicate cultures per condition.

Figure 13:
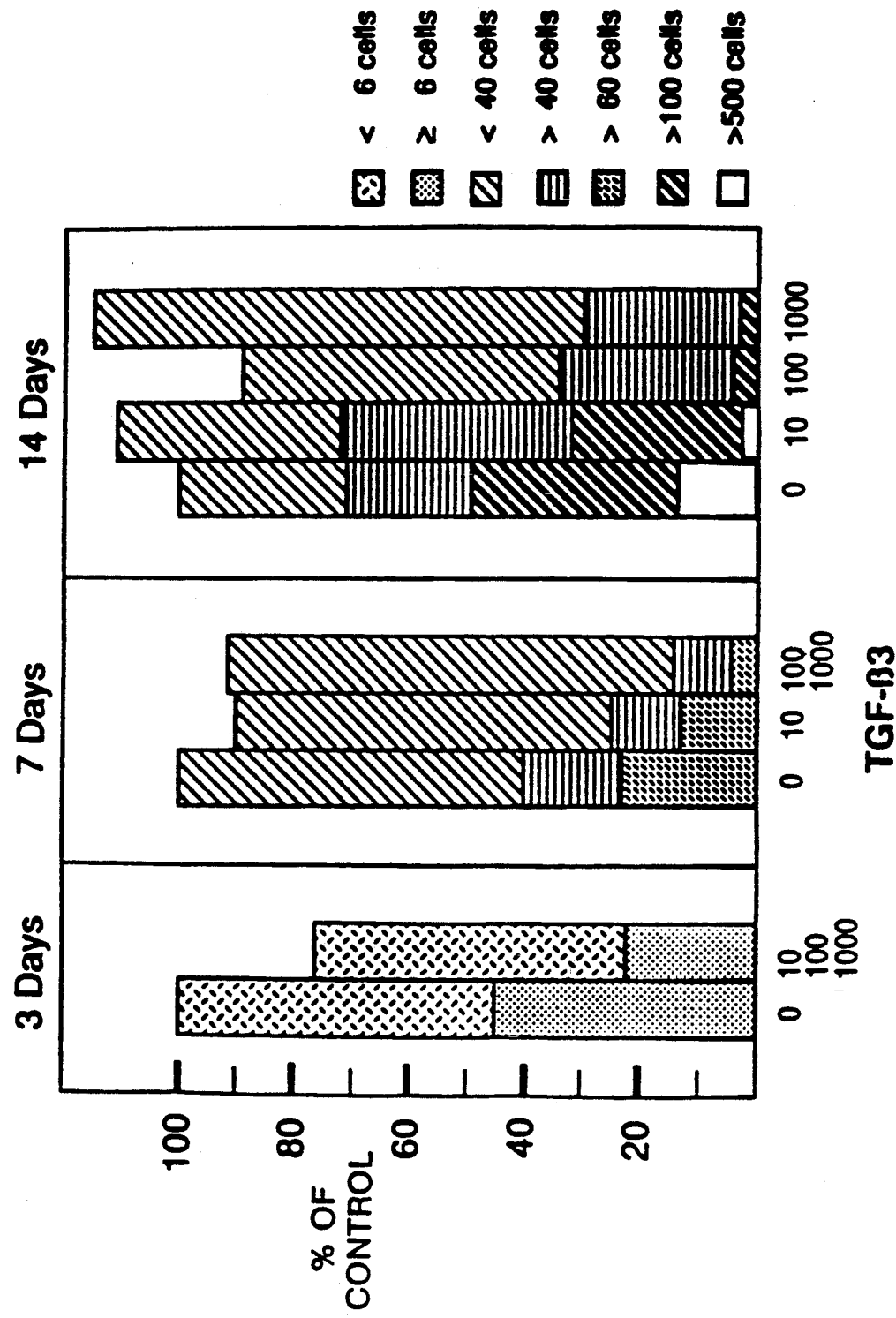

FIG. 13: Inhibition of hematopoietic stem cells by TGF-β3. Primary bone marrow cells were enriched for a progenitor stem cell population by immunodepletion and cultured as described. Cells were grown in the presence of Mo-T Cell conditioned media and increasing concentrations of purified TGF-β3 (0, 10, 100, 1000) and colony sizes determined at 3, 7 and 14 days. TGF-β3 inhibited proliferation and subsequent increase in hematopoietic colony size in a dose and time dependent manner.

FIGS. 14A and 14B: Evaluation of TGF-β3 as an chemoprotective agent in vitro - Mink cells were seeded in 96-well plates at $10^3$ cells/well in 100 μl of DMEM supplemented with 10% fetal bovine serum. Well's containing treated cells received 25 μl of TGF-β3 (50 ng/ml). After 24 hr incubation with TGF-β3, 25 μl of colchicine or vinblastine was added. After another 24 hrs, the media was removed and the cells washed once with Dulbeccol's PBS and fresh complete media added. The cells were incubated for another 7 days. Cell growth was quantitated by uptake of $^{125}$I-iodo-2'deoxyuridine as previously described.

DETAILED DESCRIPTION OF THE INVENTION

Figures 1, 14:
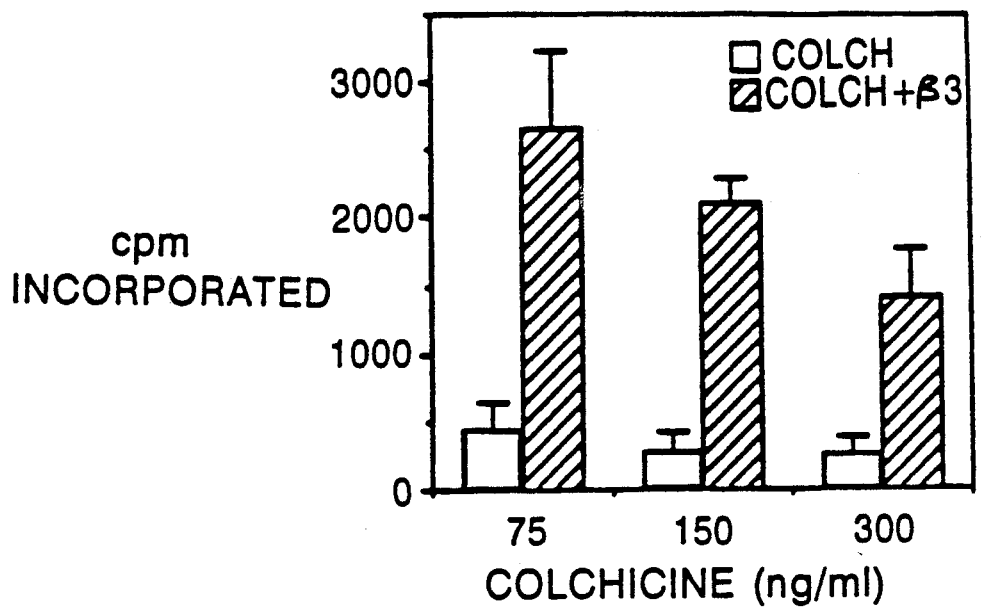
FIG. 1 shows the nucleotide sequence encoding TGF-β3 and its deduced amino acid sequence. Putative glycosylation sites and polyadenylation signals are underlined. The start of the mature TGF-β3 is marked by an asterisk at nucleotide positions 1163-1165.
Figures 2, 14:
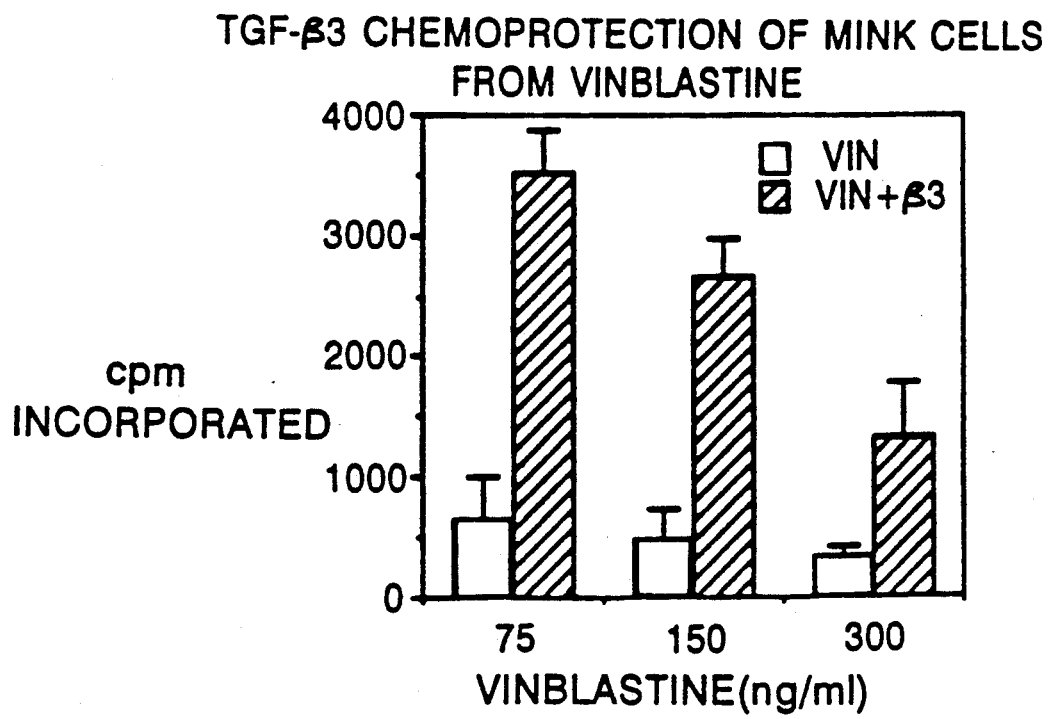

In accordance with the invention, mature TGF-β3 is defined as a recombinant homodimeric protein which comprises two polypeptides each of which consists essentially of 112 amino acids and has a sequence substantially identical to the amino acid sequence shown in FIG. 1 beginning with an alanine encoded by nucleotides 1163–1165 and ending with a serine encoded by nucleotides 1496–1498.

Moreover, as used herein TGF-β3 precursor is a recombinant homodimeric protein which comprises two polypeptides, each polypeptide encoded by a sequence substantially identical to the amino acid sequence shown in FIG. 1 beginning with a methionine encoded by nucleotides 263–265 and ending with a serine encoded by nucleotides 1496–1498.

Further, as used herein the pro region of the TGF-β3 precursor is a recombinant protein which comprises the TGF-β3 precursor without the mature TGF-β3. Additionally, the pro region of the TGF-β3 precursor is a protein region encoded by a sequence substantially identical to the amino acid sequence shown in FIG. 1 beginning with a methionine encoded by nucleotides 263–265 and ending with an arginine encoded by nucleotides 1160–1162.

Also, as used herein, reference to TGF-β means either mature TGF-β (e.g. TGF-β1, -β2, -β3), TGF-β precursor (e.g. TGF-β1 precursor, TGF-β2 precursor, TGF-β3 precursor) , or the pro region of the TGF-β (e.g. TGF-β1, -β2, -β3) precursor.

Antibodies directed to mature TGF-β have previously been described. However, these antibodies exhibit substantial cross reactivity to various TGF-β isoforms because of the high homology between them. Surprisingly, the antibody, disclosed herein, is specifically directed to mature TGF-β3 and displays no substantial cross reactivity with other TGF-β isoforms.

The present invention provides an antibody (for example a monoclonal or a polyclonal antibody) which (a) specifically binds to human TGF-β3 and (b) exhibits substantially no cross reactivity with TGF-β3 or TGF-β2. In one embodiment of the invention, the antibody may be directed to an epitope defined by the amino acid sequence DTNYCFRNLEENC. In another embodiment, the subject antibody is directed to an epitope defined by the amino acid sequence YLR-SADTTHSTVLGLYNTLNPEASASY.

Generally, an antibody comprises two molecules, each molecule having two different polypeptides, the shorter of which functions as the light chains of the antibody and the longer of which polypeptides function as the heavy chains of the antibody. However, as used herein, antibody is given a functional definition, i.e. any molecule, whether naturally-occurring, artificially induced, or recombinant, which has specific immunoreactive activity. Normally, as used herein, an antibody will include at least one variable region from a heavy or light chain (37–43).

Accordingly, a fragment of a naturally occurring or recombinant antibody molecule is encompassed within the scope of this invention. As used herein a Fab protein or a F(ab')2 protein which exhibits immunoreactive activity is an antibody.

This invention further provides an antibody which (a) specifically binds to a pro region of the TGF-β3 precursor and (b) exhibits substantially no cross reactivity with mature TGF-β3.

In one example of the invention, the subject antibody which (a) specifically binds to a pro region of the TGF-β3 precursor is directed to an epitope defined by the amino acid sequence GDILENIHEVMEIKRKGVD-NEDD (Table 1). In another example, the subject antibody is directed to an epitope defined by the amino acid sequence GDILENIHEVMEIK (Table 1). In yet a further example, the subject antibody is directed to an epitope defined by the amino acid sequence EEMH-GEREEGCTQENTESEY (Table 1) .

Additionally, the present invention provides a method of detecting a TGF-β3 precursor from a sample. The method comprises contacting the sample with a suitable amount of the above-described antibody, under conditions such that the antibody binds to the TGF-β3 precursor and detecting the antibody bound to the TGF-β3 precursor and thereby detecting the TGF-β3 precursor from the sample.

Further, the present invention provides a method of detecting a pro region of a TGF-β3 precursor from a sample which comprises contacting the sample with a suitable amount of the above-described antibody, under conditions such that the antibody binds to the pro region of the TGF-β3 precursor and detecting the antibody bound to the pro region of the TGF-β3 precursor and thereby detecting the pro region of the TGF-β3 precursor from the sample.

The present invention also provides a method of diagnosing a disorder associated with a variation in a TGF-β levels in a human subject. The method comprises (1) obtaining a sample from the subject, (2) detecting the presence of the TGF-β in the sample, and (3) determining the amount of TGF-β in the sample thereby diagnosing the disorder. In accordance with the invention, the disorder may be any disorder selected from a group including, but not limited to, osteoporosis, an immunosuppressive disease, a bone disorder, an AIDS viral infection, a dermatological disorder,, myocardial ischemia, a myopathic disorder, a connective tissue disorder, or a neurological disorder.

Further, in accordance with the above-described method, the TGF-$\beta$ may be TGF-$\beta$1. Alternatively, the TGF-$\beta$ may be TGF-$\beta$2. Further alternatively, the TGF-$\beta$ may be TGF-$\beta$3. TGF-$\beta$3 is preferred.

In one example of the above-described method, when TGF-$\beta$ is mature TGF-$\beta$3, detection of the variation in mature TGF-$\beta$3 levels may be effected by an antibody which specifically binds to mature TGF-$\beta$3 and exhibits substantially no cross reactivity with mature TGF-$\beta$3 or mature TGF-$\beta$2. Alternatively, detection may be effected by an antibody which specifically binds to the pro region of human TGF-$\beta$3 precursor and exhibits substantially no cross reactivity with mature TGF-$\beta$3.

TGF-$\beta$3 is a bifunctional growth factor. The experiments disclosed herein illustrate that TGF-$\beta$3 inhibits or stimulates the same target cell depending upon the quality of exposure to and concentration of other exogenous factors. As a potent modulator of cell growth and differentiation, the regulation of TGF-$\beta$3 levels in concert with other exogenous factors is important for normal tissue function and development.

This invention provides a method for treating a subject suffering from a disorder associated with a TGF-$\beta$ which comprises administering to the subject an amount of an antibody which specifically recognizes TGF-$\beta$ and neutralizes TGF-$\beta$ activity.

In accordance with the above-described invention, the method includes treating a subject suffering from cancer which comprises administering to the subject an amount of an antibody which specifically recognizes TGF-$\beta$ and neutralizes TGF-$\beta$ activity.

Additionally, the method includes treating a subject suffering from arthritis which comprises administering to the subject an amount of an antibody which specifically recognizes TGF-$\beta$ and neutralizes TGF-$\beta$ activity.

Further, this method further includes treating a subject suffering from an immune-suppressive disease which comprises administering to the subject an amount of an antibody which specifically recognizes TGF-$\beta$ and neutralizes TGF-$\beta$ activity.

The subject method also includes treating a subject suffering from an AIDS viral infection. The method comprises administering to the subject an amount of an antibody which specifically recognizes TGF-$\beta$ and neutralizes TGF-$\beta$ activity.

Also, the method includes treating a subject suffering from myocardial ischemia. The method comprises administering to the subject an amount of an antibody which specifically recognizes TGF-$\beta$ and neutralizes TGF-$\beta$ activity.

This method further includes treating a subject suffering from a myopathic disorder which comprises administering to the subject an amount of an antibody which specifically recognizes TGF-$\beta$ and neutralizes TGF-$\beta$ activity.

Also, this method includes treating a subject suffering from a connective tissue disorder which comprises administering to the subject an amount of an antibody which specifically recognizes TGF-$\beta$ and neutralizes TGF-$\beta$ activity.

Additionally, this method includes treating a subject suffering from a atherosclerosis. The method comprises administering to the subject an amount of an antibody which specifically recognizes TGF-$\beta$ and neutralizes TGF-$\beta$ activity.

The present method includes treating a subject suffering from a neurological disorder which comprises administering to the subject an amount of an antibody which specifically recognizes TGF-$\beta$ and neutralizes TGF-$\beta$ activity.

Additionally, the method includes treating a subject suffering from a bone disorder which comprises administering to the subject an amount of an antibody which specifically recognizes TGF-$\beta$ and neutralizes TGF-$\beta$ activity.

In one example of the above-described methods of treatment, the antibody (e.g. a polyclonal, preferably a monoclonal antibody) is an antibody which specifically recognizes mature TGF-$\beta$ and exhibits substantially no cross reactivity with the pro region of the TGF-$\beta$ precursor. In another example, the antibody is an antibody which specifically binds to mature TGF-$\beta$3 and exhibits substantially no cross reactivity with mature TGF-$\beta$1 or mature TGF-$\beta$2. In another example of the invention, the antibody may be a humanized antibody. In alternative examples, the antibody may be in the form of a F(ab) fragment or a F(ab')2 fragment.

As used herein, a humanized antibody includes structurally engineered antibodies comprising a polypeptide containing a human constant region or engineered such that they are made non-immunogenic in humans by one skilled in the art (37, 38, 39, 40, 41, 42, 43).

The present invention also provides a pharmaceutical composition comprising an effective amount of a pro region of a TGF-$\beta$ precursor and a suitable pharmaceutical carrier. In one example of the subject pharmaceutical composition the pro region of the TGF-$\beta$ precursor is the pro region of the TGF-$\beta$1 precursor. Alternatively, in another example the pro region of the TGF-$\beta$ precursor is the pro region of the TGF-$\beta$2 precursor. In a preferred example, the pro region of the TGF-$\beta$ precursor is the pro region of the TGF-$\beta$3 precursor.

Moreover, this invention also provides a method for treating a subject suffering from a cancer which comprises administering to the subject an amount of the above-described pharmaceutical composition so as to alleviate the symptoms of the cancer and thereby treating the subject.

Also, the invention provides a method for treating a subject suffering from a connective tissue disorder which comprises administering to the subject an amount of the above-described pharmaceutical composition so as to alleviate the symptoms of the disorder and thereby treating the subject.

The invention additionally provides a method for treating a subject suffering from a neurological disorder which comprises administering to the subject an amount of the above-described pharmaceutical composition so as to alleviate the symptoms of the disorder and thereby treating the subject.

Also, this invention provides a method for treating a subject suffering from an immunosuppressive disorder which comprises administering to the subject an amount of the previously-described pharmaceutical composition so as to alleviate the symptoms of the disorder and thereby treating the subject.

Furthermore, the invention provides method for treating a subject suffering from a bone disorder associated with a TGF-$\beta$ which comprises administering to the subject an amount of the previously-described pharmaceutical composition so as to alleviate the symptoms of the disorder and thereby treating the subject.

Additionally, the present invention also provides a method for treating a subject suffering from myocardial ischemia which comprises administering to the subject an amount of the previously-described pharmaceutical composition so as to alleviate the symptoms of myocardial ischemia and thereby treating the subject.

This present invention also provides a method for treating a subject suffering from a myopathic disorder which comprises administering to the subject an amount of the above-described pharmaceutical composition so as to alleviate the symptoms of the disorder and thereby treating the subject.

Additionally, the invention provides a method for treating a subject suffering from atherosclerosis. The method comprises administering to the subject an amount of the above-described pharmaceutical composition so as to alleviate the symptoms of atherosclerosis and thereby treating the subject.

Also, this invention provides a method for treating a subject suffering from arthritis. The method comprises administering to the subject an amount of the above-described pharmaceutical composition so as to alleviate the symptoms of arthritis and thereby treating the subject.

This invention further provides a method for treating a subject suffering from an AIDS viral infection. The method comprises administering to the subject an amount of the above-described pharmaceutical composition so as to alleviate the symptoms of the infection and thereby treating the subject.

Further, this invention additionally provides a method for treating a subject suffering from a disorder associated with a TGF-$\beta$ which comprises administering to the subject an amount of mature TGF-$\beta$3 so as to alleviate the symptoms of the disorder and thereby treating the subject.

In accordance with the practice of the invention, the method includes treating a subject suffering from a connective tissue disorder. The method comprises administering to the subject an amount of mature TGF-$\beta$3 so as to alleviate the symptoms of the disorder and thereby treating the subject.

Moreover, the method also includes treating a subject suffering from a neurological disorder which comprises administering to the subject an amount of mature TGF-$\beta$3 so as to alleviate the symptoms of the disorder and thereby treating the subject. In one example, the neurological disorder may be a demyelinating disease.

This method further includes treating a subject suffering from an immunosuppressive disorder which comprises administering to the subject an amount of mature TGF-$\beta$3 so as to alleviate the symptoms of the disorder and thereby treating the subject.

The present method also includes treating a subject suffering from an inflammatory disorder. The method comprises administering to the subject an amount of mature TGF-$\beta$3 so as to alleviate the symptoms of the disorder and thereby treating the subject.

This method includes treating a subject suffering from septic shock. The method comprises administering to the subject an amount of mature TGF-$\beta$3 so as to alleviate the symptoms of septic shock and thereby treating the subject.

This method also includes treating a subject suffering from a bone disorder which comprises administering to the subject an amount of mature TGF-$\beta$3 so as to alleviate the symptoms of the disorder and thereby treating the subject. Further, in accordance with the claimed method, the bone disorder may be a bone fracture.

Furthermore, the method includes treating a subject suffering from a dermatological disorder which comprises administering to the subject an amount of mature TGF-$\beta$3 so as to alleviate the symptoms of the disorder and thereby treating the subject.

The method additionally includes treating a subject suffering from myocardial ischemia which comprises administering to the subject an amount of mature TGF-$\beta$3 so as to alleviate the symptoms of myocardial ischemia and thereby treating the subject.

Additionally, the method also includes treating a subject suffering from a myopathic disorder which comprises administering to the subject an amount of mature TGF-$\beta$3 so as to alleviate the symptoms of the disorder and thereby treating the subject.

The present method additionally includes treating a subject suffering from atherosclerosis. The method comprises administering to the subject an amount of mature TGF-$\beta$3 so as to alleviate the symptoms of atherosclerosis and thereby treating the subject.

Also, the method includes treating a subject suffering from an AIDS viral infection. The method comprises administering to the subject an amount of mature TGF-$\beta$3 so as to alleviate the symptoms of the AIDS viral infection and thereby treating the subject.

Also, the present invention concerns a method for treating a subject suffering from a disorder associated with a TGF-$\beta$ which comprises administering to the subject an amount of TGF-$\beta$3 precursor so as to alleviate the symptoms of the disorder and thereby treating the subject.

In accordance with the practice of the subject invention, the method includes treating a subject suffering from a cancer which comprises administering to the subject an amount of TGF-$\beta$3 precursor so as to alleviate the symptoms of cancer and thereby treating the subject.

The present method includes treating a subject suffering from a connective tissue disorder which comprises administering to the subject an amount of TGF-$\beta$3 precursor so as to alleviate the symptoms of the disorder and thereby treating the subject.

This method further includes treating a subject suffering from a neurological disorder which comprises administering to the subject an amount of TGF-$\beta$3 precursor so as to alleviate the symptoms of the disorder and thereby treating the subject. In one example of the invention, the neurological disorder is a demyelinating disease.

The subject method additionally includes treating a subject suffering from an immunosuppressive disorder which comprises administering to the subject an amount of TGF-$\beta$3 precursor so as to alleviate the symptoms of the disorder and thereby treating the subject.

Additionally, this method includes treating a subject suffering from an inflammatory disorder which comprises administering to the subject an amount of TGF-$\beta$3 precursor so as to alleviate the symptoms of the disorder and thereby treating the subject.

Further, this method includes treating a subject suffering from septic shock which comprises administering to the subject an amount of TGF-$\beta$3 precursor so as to alleviate the symptoms of septic shock and thereby treating the subject.

The present method includes treating a subject suffering from a bone disorder which comprises administering to the subject an amount of TGF-β3 precursor so as to alleviate the symptoms of the disorder and thereby treating the subject. In one example, the bone disorder is a bone fracture.

Additionally, the present method also includes treating a subject suffering from a dermatological disorder which comprises administering to the subject an amount of TGF-β3 precursor so as to alleviate the symptoms of the disorder and thereby treating the subject.

Also, this method includes treating a subject suffering from myocardial ischemia which comprises administering to the subject an amount of TGF-β3 precursor so as to alleviate the symptoms of myocardial ischemia and thereby treating the subject.

This method additionally includes treating a subject suffering from a myopathic disorder which comprises administering to the subject an amount of TGF-β3 precursor so as to alleviate the symptoms of the disorder and thereby treating the subject.

Further, this method also includes a method for treating a subject suffering from atherosclerosis which comprises administering to the subject an amount of TGF-β3 precursor so as to alleviate the symptoms of atherosclerosis and thereby treating the subject.

Additionally, this method includes a method for treating a subject suffering from an AIDS viral infection which comprises administering to the subject an amount of TGF-β3 precursor so as to alleviate the symptoms of the AIDS viral infection and thereby treating the subject.

The present invention also provides a method of obtaining bone marrow substantially free of actively dividing tumor cells which comprises: (a) contacting bone marrow containing normal hematopoietic cells and actively growing tumor cells with an effective amount of a TGF-β such that the growth of the normal hematopoietic cells is temporarily inhibited; (b) subsequently contacting bone marrow with a tumor inhibiting drug under such conditions to permanently prevent growth of tumors cells; and (d) culturing bone marrow so as to permit growth of normal hematopoietic cells thereby obtaining bone marrow substantially free of actively dividing tumor cells. In accordance with the subject invention, the TGF-β may be TGF-β1, TGF-β2, or TGF-β3. TGF-β3 is preferred.

Additionally, the present invention provides a method of obtaining bone marrow substantially free of actively dividing tumor cells. The method comprises (a) contacting bone marrow containing normal hematopoietic cells and actively growing tumor cells with an effective amount of a TGF-β; (b) culturing bone marrow of step (a) in the presence of TGF-β for a suitable period, under conditions such that terminal cell differentiation and clearance of tumor cells is permitted; and (e) obtaining bone marrow substantially free of actively growing tumor cells. In accordance with the claimed methods, the TGF-β may be TGF-β1, TGF-β2, or TGF-β3. TGF-β3 is preferred.

Finally, the invention provides a method of inhibiting cytotoxic poisoning of normal cells caused by chemotherapeutic agents in which comprises contacting normal cells with an amount of a TGF-β3 under conditions such that normal cell growth in the presence of chemotherapeutic agents is temporarily inhibited thereby inhibiting cytotoxic poisoning of normal cells.

This invention is illustrated in the Experimental Details section which follows. This section is set forth to aid an understand of the invention but is not intended to, and should not be construed to, limit in any way the invention as set forth in the claims which follow.

EXPERIMENTAL DETAILS

Abbreviations and Technical Terms:

AL (acute leukemia)
ANLL (adult non-lymphocytic leukemia)
APRT (adenosylphosphoribosyl transferase)
BFU-E (burst forming unit-erythroid)
BSA (bovine serum albumin)
CL (chronic leukemia)
CLL (chronic lymphocytic leukemia)
CML (chronic myelogenous leukemia)
CNBr (cyanogen bromide)
CFU (colony forming unit)
CFU-E (colony forming unit-erythroid)
CFU-GEMM (colony forming unit-granulocyte, erythroid, macrophage, monocute)
CFU-GM (colony forming unit-granulocyte/macrophage)
CFU-meg (colony forming unit-megakaryocyte)
CHO (chinese hamster ovary)
CMV (cytomegalovirus)
CSF (colony stimulating factor)
DHFR (dihydrofolate reductase)
DMEM (Dulbeccols modified Eagle's medium)
DMF (dimethyl formamide)
DMSO (dimethyl sulfoxide)
DNA (deoxyribonucleic acid)
EPO (erythropoietin)
FCS (fetal calf serum)
G-CSF (granulocyte-colony stimulating factor)
GM-CSF (granulocyte/macrophage-colony stimulating factor)
kb (kilobase pairs)
kDa (kilo Daltons)
HPLC (high pressure liquid chromatography)
IL-3 (interleukin-3)
IL-4 (interleukin-4)
MEM (modified Eagle's medium)
mRNA (messenger ribonucleic acid)
RNA (ribonucleic acid)
TGF-β (transforming growth factor-beta)
TIF (tumor inhibitory factor)
WBC (white blood cell)

EXAMPLE 1

Expression of TGF-β3

TGF-β3 Expression Construct

Figure 2:
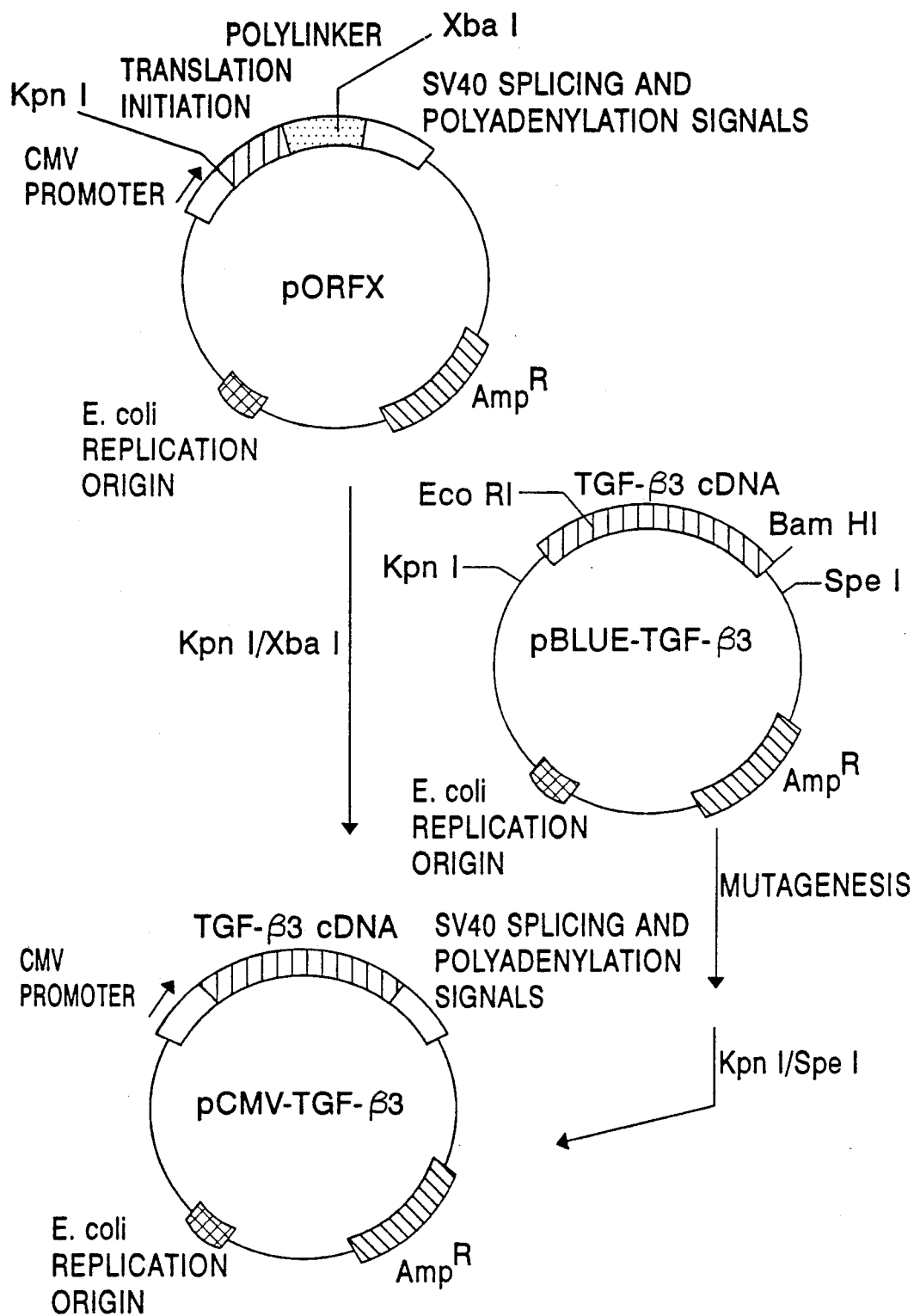
FIG. 2 is a schematic representation of the construction of the pCMV-TGF-β3 expression plasmid from PORFX and pBlue-TGF-β3 plasmids.

A 1500 bp AluI-HgaI restriction fragment of TGF-β3 CDNA (sites are indicated in FIG. 1) which encodes the complete TGF-β3 protein was cloned into the Bluescript plasmid (Strategene, La Jolla, Calif.) to yield the plasmid pBlue-TGF-β3. The f1 intergenic region of this vector allows the production of single stranded DNA via infection of its host bacteria with f1 helper phage. The initiation codon of TGF-β3 does not form part of a Kozak consensus sequence (CCACC[ATG]G) (11), which has been shown to influence the efficiency of translation. In order to promote high yields of the recombinant TGF-β3 protein, the flanking sequence of the initiation codon was mutagenized to a more efficient translation sequence by changing CACAC[ATG]A into CCACC[ATG]A using the method of Nakamaye and Eckstein (15). Mutagenesis was confirmed by sequence analysis. Expression yields are further optimized by deletion of TGF-β3 5' and 3' untranslated [non-coding] sequences. Subsequently, the mutagenized pBlue-TGF-β3 was cut with KpnI and SpeI, two polylinker restriction sites flanking the CDNA insert. This fragment was cloned into the eucaryotic expression vector PORFEX (1) cut with KpnI and XbaI. In this construct (pCMV:TGF-β3) the TGF-β3 CDNA sequence is transcriptionally regulated by the cytomegalovirus immediate early promoter (FIG. 2).

DNA Transfection and Gene Amplification

Stable transformants expressing TGF-β3 were obtained by cotransfecting the pCMV-TGF-β3 construct (FIG. 2) with the dihydrofolate reductase (DHFR) gene (the PDCHIP plasmid containing hamster DHFR minigene driven by its own promoter) into Chinese Hamster Ovary (CHO) cells, which lack the DHFR gene (19).

A standard $CaPO_4$.DNA precipitation method (8) was used for DNA transfection. pCMV:TGF-β3 (5.7 kb) and PDCHIP (2.5 kb) were coprecipitated with $CaPO_4$ in a ratio of 10 μg to 50 ng respectively and the precipitate added to $0.5 \times 10^6$ CHO (DHFR-) cells. Selection of transformants with a DHFR+ phenotype was performed in alpha MEM (Gibco, Grand Island, N.Y.) supplemented with 10% dialyzed fetal calf serum. The colonies that appeared after culturing for 10-14 days in selection medium were isolated by standard methods and expanded.

Figure 3:
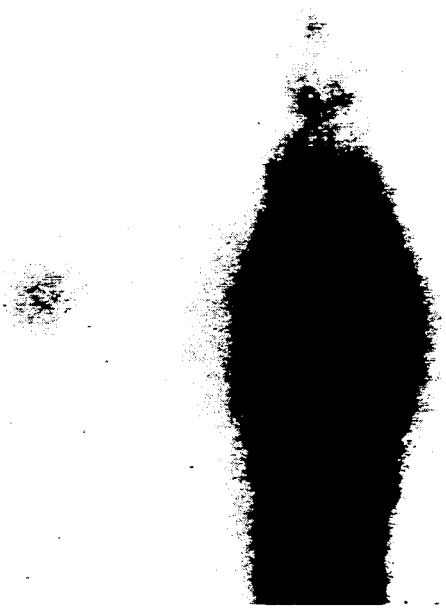
FIG. 3 shows the level of TGF-β3 MRNA expression, determined by Northern hybridization using a TGF-β3 specific probe, of parental CHO cells (lane 1), CHO cells transfected with TGF-β3 cDNA (CHO 6.35) (lane 2) and CHO 6.35 amplified with 20 nM MTX (CHO 6.35/20 nM (lane 3).
Figure 4:
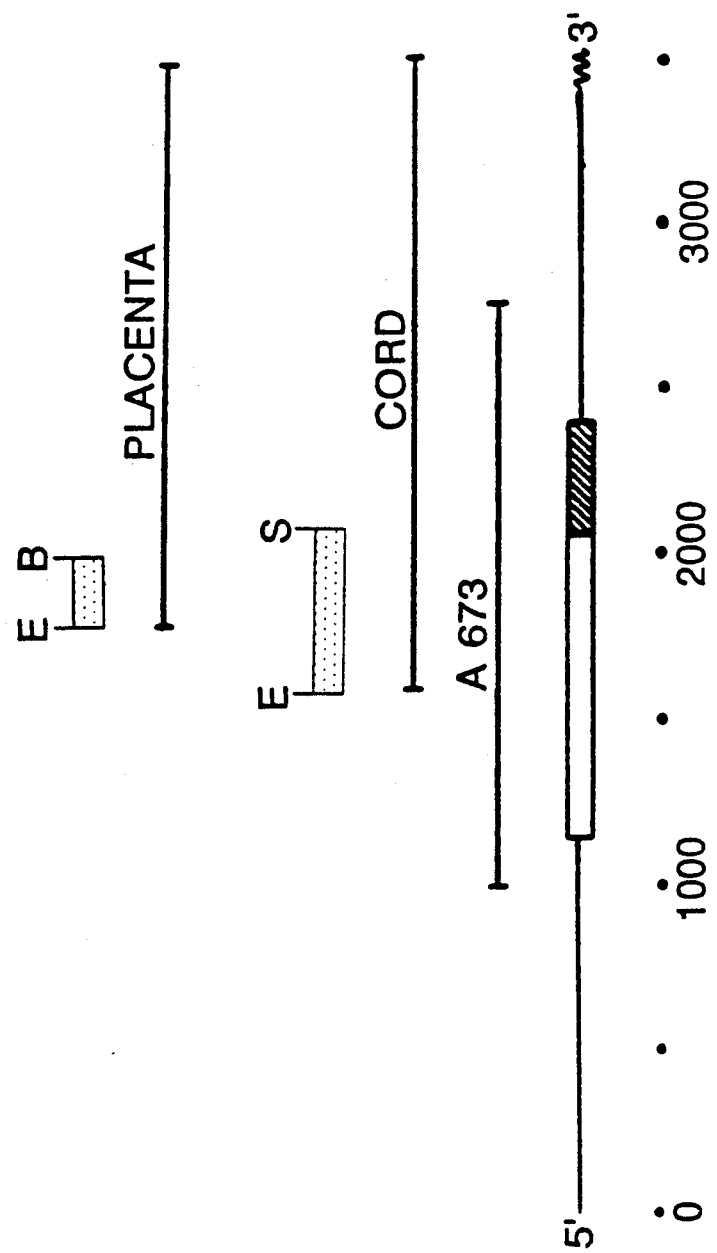
FIG. 4 shows a schematic diagram of MRNA encoding TGF-β3 with the coding sequence boxed. The relative extension of the cDNA inserts obtained from placenta (1.7 kb), umbilical cord (1.9 kb) and A673 (1.7 kb) libraries is indicated. The dashed part of the box represents the C-terminal region showing high homology to TGF-βs. The 5' EcoRI-Bg II restriction fragment of the placenta CDNA is indicated by a bar.

For gene amplification, the primary transfectants were subjected to stepwise selection with increasing concentrations of methotrexate (MTX; Sigma Chemical Co., St. Louis, Mo.). The first round of selection was carried out at 20 nM MTX. TGF-β3 expression levels were measured by RNA cytodot hybridization normalizing the expression of TGF-β3 MRNA to that of actin. Two of the three clones with initial high expression (clones CHO 6.35 and CHO 9.1) showed increased TGF-β3 MRNA expression at 20 nM MTX concentration (FIG. 3). Total RNA (75 μg) from CHO cells (lanes 1), CHO 6.35 (lane 2), and CHO 6.35/20 nM (lane 3), were fractionated on a 1.2% agarose-formaldehyde gel, blotted onto nitrocellulose and probed with a TGF-β3 specific probe (EcoRI-SmaI CDNA restriction fragment of a partial TGF-β3 CDNA clone isolated from umbilical cord; see FIG. 4). CHO 6.35/20 nM (primary transfectant CHO clone 6.35 at 20 nM MTX), which had the highest level of expression, was chosen for initial protein purification from conditioned media and for further gene amplification.

The best clone from further MTX selection (10 μM MTX) was expanded and a bank of frozen stocks established. This clone, 6.35H, was used in all subsequent production of TGF-β3 and was maintained in T225 flasks (225 $cm^2$) in alpha MEM supplemented with 10% dialyzed fetal bovine serum. TGF-β3 production involved seeding Nunc cell factories (6000 $cm^2$ of surface area per factory), with cells from three confluent T225 flasks of 6.35H in alpha MEM supplemented with 10% dialyzed FBS. The cells were allowed to grow to 80% confluence in the cell factories. Media was then replaced with HB CHO, a serum-free media from HANA (Hana Biologics, Calif.). After 72 hours, media was removed and replaced with fresh HB CHO for a total of 5 collections of conditioned HB CHO media. The first collection of conditioned HB CHO media contained low levels of TGF-β3 with the maximum amounts produced in the 4th through 6th collections. Nunc cell factories provide sufficient surface area for the large scale growth of monolayer cell lines such as CHO, yielding a total of 7.5 liters of conditioned media per factory (3 collections, 2.5 liters per collection) with acceptable ease of use in a sterile environment. Using more advanced expression vector systems, it should be possible by one skilled in the art to significantly increase production yields.

Alternatively, cell lines could be adapted to suspension growth and produced in either a stirred tank fermentation system or in an air lift fermentator. The use of porous glass cylinder supports as a means of adapting monolayer cells (i.e. CHO cells) to stirred or air-lift suspension culture has also been evaluated and shown to give acceptable yields of TGF-β3.

Expression of a mutant TGF-β3 Precursor

The mutant TGF-β3 precursor is expressed as a single homodimeric polypeptide in a host cell by mutation of the R-K-K-R cleavage site between the TGF-β3 pro region and mature TGF-β3 to a protease cleavage site, e.g. factor Xa cleavage sequence (Ile-Glu-Gly-Arg) or a collagenase cleavage sequence (Pro-X-Gly-Pro) using standard site directed mutagenesis procedures, followed by insertion of the mutant TGF-β3 nucleic acid into a expression vector and transfection of the mutant TGF-β3/vector DNA into a host cell (e.g. E. coli, CHO, or HeLa) together with DNA encoding a selectible marker (e.g. neo, dhfr).

Biological Assay for Conditioned Media

Conditioned media was treated with acetic acid to a final concentration of 0.1M and serial dilutions tested for biological activity. CCL 64, a cell line derived from Mink lung (American Type Culture Collection, Rockville, Md.), was found to be extremely sensitive to the naturally occurring TGF-β3 isolated from umbilical cord. This cell line was initially chosen, therefore, to test conditioned media for biological activity of the recombinant TGF-β3 protein according to the method of Iwata, et al. (10). Growth inhibition of CCL 64 mink lung cells produced by TGF-β1 (purified or TGF-β3 (from conditioned media) is shown in FIGS. 5A and 5B.

Figure 5A:
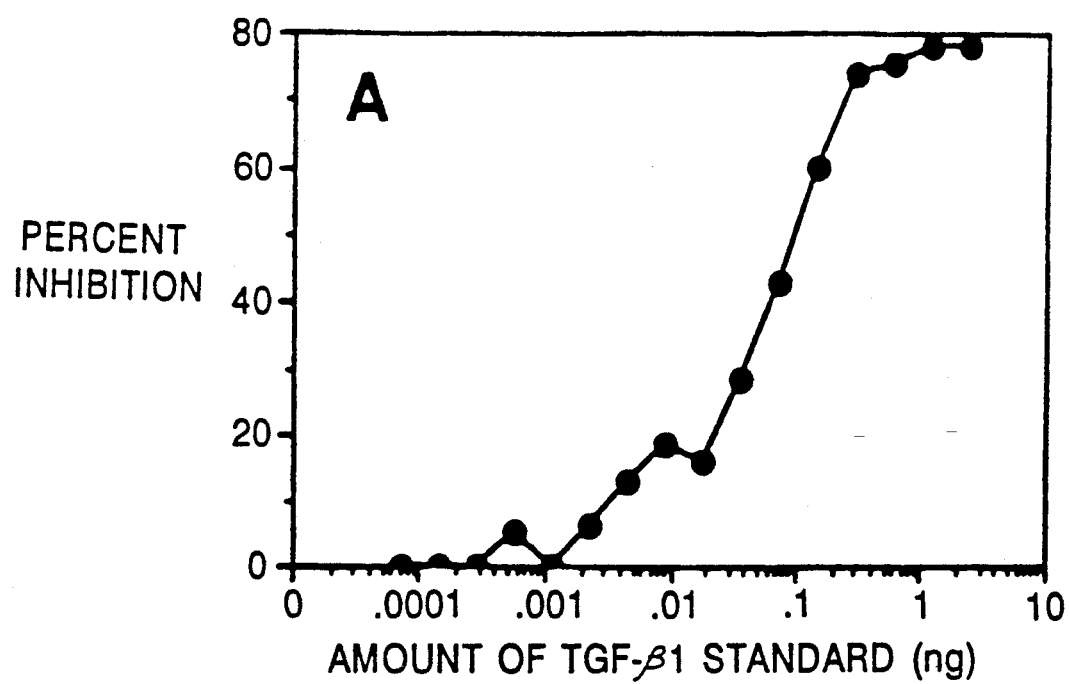
FIGS. 5A AND 5B (A) shows the dose response of mink cell growth inhibition using purified TGF-β1. Cell growth was quantitated by the metabolism of MTT 3-[4,5-Dimethylthiazol-2-yl]-2,5-diphenyltetraazolium bromide; Thiazolyl blue).
Figure 5B:
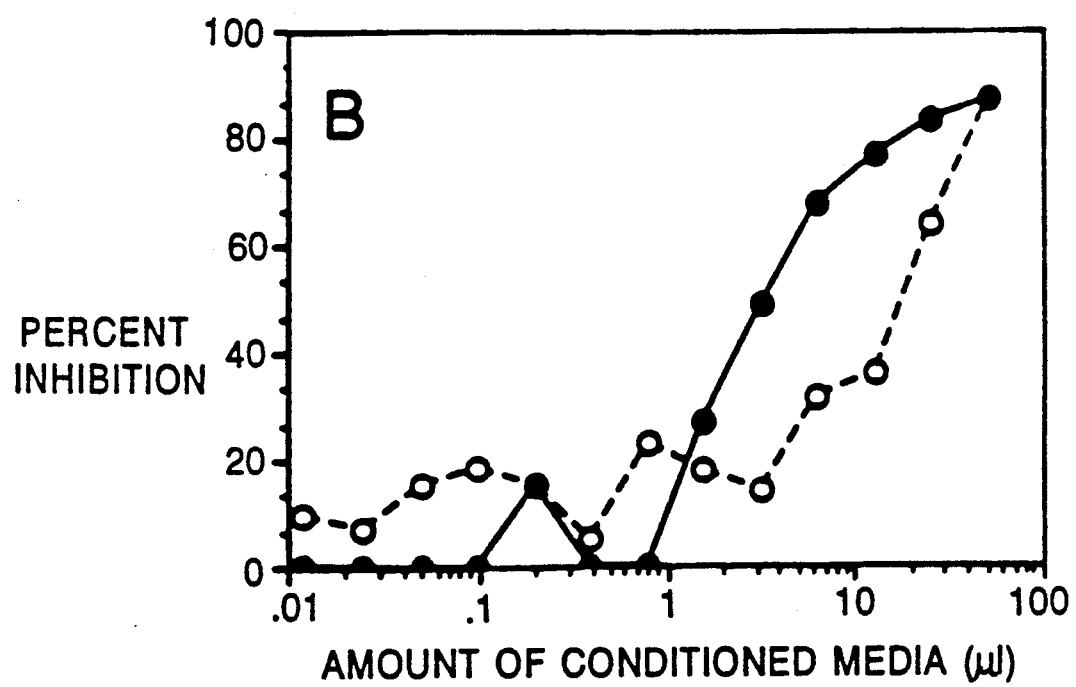

FIG. 5A shows a dose response of growth inhibition using purified TGF-β1 (Calbiochem); a 50% inhibition was obtained with 0.1 ng TGF-β1. An increase in mink cell growth inhibitory activity was found comparing conditioned media form the transfectant selected at 20 nM MTX versus media from the parental transfectant. FIG. 5B shows the biological activity of acid activated serum free supernatants of CHO 6.35/20 nM transfectant (closed circles) and CHO 6.35 transfectant (open circles); 50% inhibition was obtained equivalent to 30 and 5 ng/ml TGF-β1 activity, respectively. Conditioned medium from parental CHO (DHFR-) possessed much lower growth inhibition than either transfectant. These results clearly indicate that the TGF-β3 CDNA is transcribed and that TGF-β3 MRNA is translated and produces biologically active protein.

In the presence of EGF, acidified conditioned media from CHO 6.35, containing TGF-β3 was able to promote soft agar growth of NRK cells. Growth of NRK cells in soft agar has been shown to be inducible by stimulating the production of extracellular matrix proteins, an important parameter in wound healing.

Immunodetection

Peptides corresponding to various partial amino acid sequences of the TGF-β3 protein were synthesized on an Applied Biosystems peptide synthesizer (Model 430A) using tBoc chemistry (FIG. 6). Peptides were coupled to keyhole limpet hemocyanin with glutaraldehyde and used for immunization of rabbits. Enzyme-linked immunosorbent assays were used initially to characterize the antibody titers (Table 1). For this, and the following immunological experiments, standard techniques were employed (9). High titer antibody from immunized rabbits injected with β3V or β3III peptides were purified using an affinity matrix composed of the respective peptide β3 antigen conjugated to Affi-prep 10 (Bio Rad, Richmond, Calif.).

TABLE 1

| Peptide | Sequence | Elisa Titer |
| --- | --- | --- |
| I | EEMHGEREEGCTQENTESEY | 1:6,000 |
| IIL | GDILENIHEVMEIKRKGVDNEDD | 1:10,000 |
| IIs | GDILENIHEVMEIK | 1:19,000 |
| III | DTNYCFRNLEENC | 1:26,000 |
| IV | CVRPLYIDFRQDLGWKWVHEPKGYYANFC | 1:19,000 |
| V | YLRSADTTHSTVLGLYNTLNPEASASY | 1:26,000 |
| VI | CVPQDLEPLTILYYVGRTPKVEQLSNMVVKSC | 1:4,000 |

The affinity purified β3III antibody exhibits greater than 300 fold specificity for the β3III peptide compared to the cognate peptide sequences from either the TGF-β1 or -β2. Furthermore, no significant cross reactivity of this antibody has been observed against either the TGF-β1 or -β2 proteins. However, this antibody shows only a very limited ability to immunoprecipitate the native recombinant TGF-β3 protein from conditioned media. The affinity purified β3V antibody exhibits at least a 400-fold selectively for the β3V peptide compared to the corresponding peptide sequence form TGF-β1. This antibody can also efficiently immunoprecipitate the native TGF-β3 protein (FIG. 7).

FIGS. 8A and 8B show an immunoblot of TGF-β3 in conditioned media produced by the CHO 6.35/20 nM transfectant using β3 III and β3V antibodies for detection. For peptide blocking experiments, the antibody was preincubated with 80-fold molar excess of peptide prior to incubation with the blot. For detection, alkaline phosphatase (Zymed, San Francisco, Calif.) conjugated to goat anti-rabbit IgG was used as a second antibody. FIG. 8A shows a Western blot of a gel where the sample was subjected to reduction prior to electrophoresis while FIG. 8B shows the Western blot of the sample under non-reducing conditions. In each figure, lanes 1–3 and 4–6 corresponds to conditioned media immunoblotted with β3V and β3III antibody, respectively, lanes 2 and 5 immunoblots carried out in the presence of excess cognate peptide, while lanes 3 and 6 represent immunoblots in the presence of an excess unrelated peptide sequence.

Western blotting of conditioned media from CHO 6.35/20 nm cells under reducing conditions, using affinity purified β3III and β3V antibody, detected a 50 kDa and a 12 kDa band. These bands correspond to the TGF-β3 precursor and mature TGF-β3, by analogy to the processing of TGF-β1 and TGF-β2 described by Gentry et al. (6) and Madisen et al. (13) (FIGS. 8A and 8B).

Under non-reducing conditions, 100 kDa and 24 kDa bands were observed, which we believe to correspond to homodimeric forms of the TGF-β3 precursor and mature TGF-β3. The apparent precursor appears as a broad band, characteristic of some glycosylated proteins. Following cleavage of the signal peptide sequence of the precursor form of TGF-β3, one would expect a protein with MW of 43 kDa (under reduced conditions).

Based on the primary sequence of TGF-β3, there are four N-linked glycosylation sites, further indicating that the detected precursor protein is glycosylated. FIGS. 9A and 9B show western blot of cell extract (FIG. 9A) and conditioned media (FIG. 9B) of the CHO 6.35/20 nM transfectant using β3V antibody for detection. For preparation of cell extracts, cells were first washed with phosphate buffered saline then lysed directly with SDS/β-mercapthoethanol prior to gel electrophoresis. For peptide blocking (lanes 2 and 4), the antibody was incubated with a 100-fold molar excess of specific peptide prior to incubation with the blot ($^{125}I$ protein-A was used for detection). In cell extracts of CHO 6.35/20 nM under reducing conditions, only the 50 kDa band corresponding to a potential precursor form is detected (FIGS. 9A and 9B). The specificity of the antibody was demonstrated by preabsorbing the antibodies with peptide immunogen prior to Western blotting (FIGS. 8A and 8B and 9A and 9B). As expected, based on MRNA and biological activity data, the antibody did not detect any TGFβ3 protein in conditioned media of the parental CHO (DHFR-) cells.

Both antibody were also tested for immunoprecipitation of native recombinant TGF-β3 protein (FIG. 7). CHO 6.35/20 nM were grown to confluency and labeled with [$^{35}S$] methionine for 24 hours in methionine-free DMEM in the presence of 5% dialyzed plus 5% non-dialyzed fetal calf serum. The medium was collected and immunoprecipitated with 10 µg/ml affinity purified antibody and 20 µg/ml (1:2 dilution) protein A agarose, for 2 hours at 4° C. Separation of the immunoprecipitated proteins on a 12.5% SDS polyacrylamide gel revealed two proteins migrating identically to the mature TGF-β3 (12 kDa) and precursor TGF-β3 (50 kDa) (FIG. 7). However, one extra immunoprecipitated protein was found at 43 kDa.

The 43 kDa protein may correspond to either the non-glycosylated precursor or a proteolytic breakdown product. The β3V antibody, in comparison to the β3III antibody, proved to be much more efficient in immunoprecipitating the TGF-β3 protein. The specificity of the immunoprecipitation was determined by preincubating the antibody with a 80-fold molar excess of either the cognate peptide or an unrelated peptide sequence. The specific peptide showed complete competition of all three bands whereas the unrelated peptide did not. As expected, based on the amino acid composition and distribution of methionine in the TGF-β3 protein, the 50 kDa contains significantly more $^{35}S$ label.

The β3V affinity purified antibody was also used in paraffin sections of human umbilical cord (FIGS. 10A, 10B, 10C and 10D). Fibroblasts and epithelial cells stained (FIG. 10A) as did the smooth muscle fibers of the cord vasculature (FIG. 10C) whereas neither the connective tissue nor the extracellular matrix stained with this antibody. A control rabbit polyclonal antibody (Ig against P210phl/abl:OSI catalog #PCO2) showed no staining (FIGS. 10 B and D). The strong staining in umbilical cord tissue agrees with earlier data showing extracts from umbilical cord possessed high levels of MRNA.

Preparation of TGF-β3 Monoclonal Antibody

A TrpE-TGF-β3 fusion was produced in *E. coli* which had the following characteristics, i.e. amino acids 1 to 19 are coded by the TrpE and poly linker segment and amino acids 20 to 170 correspond to amino acids 273 to 412 of the TGF-β3 precursor (containing the full mature TGF-β3 sequence). The fusion protein remained in the insoluble fraction after sonication in PBS. Subsequently, the protein was purified by separation on a SDS-polyacrylamide gel and isolated by electroelution. This material was used for immunization of mice by the following protocol:
a. Balb/C female mice were immunized intraperitoneally with 100 μg of TrpE-TGF-β3 in RIBI adjuvant on days 0, 7 and 14;
b. On day 24 test bleeds indicated high titers against TrpE-TGF-β3 and purified TGF-β3 protein;
c. The mice were then boosted with 100 μg of the same antigen on days 28, 29 and 30;
d. Spleen fusions were performed the following day; and
e. Subsequent methods of hybridoma selection, culture and subcloning were performed following standard procedures (9).

Five stable hybridomas were produced and their characteristics are shown in Table 2. All of the clones produced antibodies of the IgG k class. The monoclonal antibodies immunoblotted with purified TGF-β3. All five monoclonal antibodies showed no reactivity with TGF-β1 by ELISA, but crossreacted with TGF-β2.

Analysis of the epitopes recognized by the monoclonal antibodies using TGF-β3 synthetic peptides showed that all antibodies reacted with amino acids residues 380 to 412.

EXAMPLE 2

Antibodies Which Neutralize TGF-β3 Activity

Human platelet TGF-β1 (Collaborative Research, Mass.), porcine TGF-β2 (R&D, Minn.) or purified recombinant human TGF-β3, at concentrations from 3.125 to 0.049 ng/ml, was incubated with 5 μg/ml of affinity purified polyclonal rabbit antibodies (β3V antibody and anti-TGF-β3 (R&D, Minn.) for 3 hours at 37° C. Control TGF-β3, TGF-β2 or TGF-β1 was incubated without antibodies. Growth inhibition of mink cells by antibody treated and control untreated TGF-β3, TGF-β2 or TGF-β1 was determined as described herein. FIGS. 11A, 11B and 11C show that the β3V antibody (closed squares) neutralizes the growth inhibitory activity of TGF-β3, but not TGF-β2 or TGF-β1 on mink cells relative to the growth inhibitory activity of identical concentrations of TGF-β's in the absence of antibody (open circles). Anti-TGF-β (R&D, Minn.) neutralizes TGF-β3, TGF-β2 and TGF-β1 (FIGS. 11A, 11B and 11C) (closed circles). Neither antibody had any significant effect on the growth of CCL-64 cells in the absence of TGF-β3. Antibodies against the TGF-β3 peptide β3V apparently specifically neutralizes the growth inhibitory activity of TGF-β3.

EXAMPLE 3

Evaluation of Anti-Cancer Activity In Vitro

Growth was determined using a modification of the monolayer assay for TGF-β3 described by Iwata, K.K., et al. (10). Nonleukemic cells were subcultured on 96-well tissue culture plates in 100 μl of media at a seeding density of $2 \times 10^3$ cells per well. Cells were maintained and assayed in Dulbeccol's modified Eagle's medium containing 10% fetal bovine and 2% L-glutamine. These cells were treated with 25 ng/ml (~1 nM) of TGF-β3, pulsed 24 hours with 1 μCi/ml 5-[$^{125}$I]-iodo-2'deoxyuridine when cells in the untreated control wells were 90% confluent and harvested.

Leukemic cells (K562, KG-1, KG-1a, HuT 78 and U937) were seeded in 50 μl of media. K562 was seeded at a density of $1 \times 10^3$ cells per well in RPMI supplemented with 10% fetal bovine serum. KG-1 and KG-1a were seeded at a density of $3.5 \times 10^3$ cells per well in Iscove's media supplemented with 10% fetal bovine serum. Hut 78 and U937 were seeded at a density of $3.5 \times 10^3$ cells per cell in RPMI supplemented with 10% fetal bovine serum. Cell growth was determined by microscopic examination. Examples are shown in Table 2, showing inhibition of some human tumor lines by TGF-β3.

EXAMPLE 4

Development of Antigen Capture Assay for TGF-β3

Plates are coated with 50 μl of affinity-purified rabbit polyclonal antibody (5 μg/ml in 0.1M NaHCO₃, pH 9.1) made to TGF-β3 peptide β3V. Plates were incubated overnight at 4° C. Unbound antibody is removed by aspiration. Plates are blocked with 100 μl PBS containing 1% BSA (PBS-BSA) for 1 hr at room temperature. The plates are then washed twice with phosphate-buffered saline (PBS) containing 0.05% Tween 20 (PBST).

Samples in a final volume of 50 μl of PBS-BSA are added to the appropriate wells and incubated for 1 hr at room temperature. Unbound protein is removed and the plate is washed four times with PBST. All wells receive 50 μl of mouse monoclonal antibody against TGF-β3 (5 μg/ml in PBS). After incubation for 1 hr at room temperature, unbound antibody is removed and the plate is washed four times with PBST. All wells receive 50 μl of an appropriate dilution of alkaline phosphatase conjugated to goat anti-mouse antibody. After incubation for 1 hr at room temperature, the plate was washed four times with PBST.

Substrate for alkaline phosphatase (5-bromo-4-chloro-3-indolyl phosphate) in 100 μl is added to all of the wells and incubated for 15 min at room temperature. Absorbance in each well measured at 490 nm. Using this assay, we detected between 3-5 ng/ml recombinant TGF-β3.

EXAMPLE 5

Use of TGF-β3 in Bone Disorders

TGF-β like activities are produced by bone cells and large amounts are found in the extracellular bone matrix, indicating an important physiological function of TGF-βs in this tissue (2). TGF-β stimulates cell replication and collagen production in cultured fetal rat bone cells (3, 4, 5) and induces chondrogenesis of embryonic rat mesenchymal cells (17). In addition, molecules with TGF-β like activity are released in vitro after bone resorption and may effect a link between the coupled processes of bone formation and resorption during remodeling (16, 18).

TABLE 2

Effects of TGF-$\beta 3$ (1nM) on the Growth of Human Cell Lines in Culture

| CELL LINE | | % INHIBITION |
|---|---|---|
| Human Tumor | | |
| A549 | (lung adenocarcinoma) | 46 |
| A375 | (melanoma) | 47 |
| A2058 | (melanoma) | 88 |
| WiDR | (colon adenocarcinoma) | 24 |
| MCF 7 | (breast carcinoma) | 57 |
| Human Leukemic Cells | | |
| K562 | (CML) | 55 |
| KG-1 | (AML) | 50 |
| KG-1a | (AML) | 50 |
| HuT 78 | (T cell lymphoma) | 50 |
| U937 | (histiocytic lymphoma) | 50 |
| Normal Human | | |
| Huf | (foreskin fibroblasts) | 6 |

The experimental paradigm is to isolate various cell populations from resected bone fragments by sequential collagenase digestions (3, 4, 5). The later released populations are enriched for bone forming cells with the biochemical characteristics associated with the osteoblast phenotype, such as type I collagen production, elevated alkaline phosphatase activity and osteocalcin synthesis (14). Studies with such isolated bone cells have shown that TGF-$\beta 1$ is a potent regulator of cells from the osteoblast lineage (4). On a molar basis, TGF-$\beta 1$ is one of the most potent mitogens thus far described for osteoblast-enriched cultures from fetal bone. The mitotic response to TGF-$\beta 1$ is biphasic with an optimal concentration below 100 PM (2, 3, 4). TGF-$\beta$s, in addition, alter expression of various activities associated with the osteoblast phenotype: alkaline phosphatase activity is decreased while the synthesis of type I collagen is enhanced similar to the effects of TGF-$\beta$ in a number of other connective tissue systems (3, 4).

The experiments described below were performed to assess the effects of human recombinant TGF-$\beta 3$ on osteoblast-enriched cultures from fetal rat parietal bone and to characterize the specific binding of TGF-$\beta 3$ to bone cell-surface proteins.

Cell cultures

Parietal bones dissected free of adjacent suture lines were obtained from 22 day old rat fetuses (Sprague-Dawley, Charles River Breeding Laboratories, Wilmington, Mass.) and were subjected to 5 sequential 20 min collagenase digestions as previously described (14, 20). The population of cells released during the first enzyme treatment (population 1) is enriched with less differentiated fibroblast-like cells, whereas the last three populations (numbers 3-5) are enriched with cells expressing features characteristic of the osteoblast phenotype.

Cells from population 1 and a pool of cells from populations 3-5 were plated at 12,500 cells/cm$^2$ in 0.32 cm$^2$ wells and were cultured in Dulbecco's modified Eagle's medium as has been detailed (3, 4, 14). After reaching confluency (approximately 6-8$\times$10$^4$ cells/cm$^2$), the cultures were deprived of serum for 20 hrs; the factors of interest were then added to the cultures in serum-free medium and incubated for an additional 23 hours.

DNA synthesis

To examine the mitogenic effect of the test factors, cell cultures were pulse labeled with [$^3$H]thymidine (80 Ci/mmol) for the last 2 hours of treatment and lysed by the addition of 0.1M sodium dodecyl sulfate and 0.1N sodium hydroxide. The insoluble material formed by precipitation with 10% TCA was collected on glass fiber filters, rinsed with ethanol and measured by scintillation counting. Data are shown as the total amount of acid-precipitable [$^3$H]thymidine incorporated per 0.32 cm$^2$.

Protein synthesis

To measure collagen and noncollagen protein synthesis, 2 cm$^2$ cultures were pulsed with 12.5 $\mu$C/ml [$^3$H]proline (125 mCi/mmol) for the last 2 hours of culture. Cells were rinsed with isotonic buffer (146 mM NaCl, 11 mM dextrose, 35 mM Tris-HCl pH 7.4) and lysed by freeze-thawing in 0.5% (v/v) TRITON X-100 (detergent) (Sigma). The homogenates were diluted 3-fold, precipitated with 10% trichloroacetic acid, and the acid-precipitable material collected by centrifugation. The pellets were acetone-extracted, dried, resolubilized in 0.5M acetic acid and neutralized with NAOH. The amount of [$^3$H]proline incorporated into collagenase-digestible protein and noncollagen protein was measured as described (23).

Alkaline Rhosphatase assay

Enzyme activity was measured in extracts prepared from 2 cm$^2$ cultures following sonication in 0.5% Triton X-100. Hydrolysis of p-nitrophenyl phosphate was measured at 410 nm after 30 min (12); data are expressed as nanomoles of p-nitrophenol released per min/mg protein.

Biological activity of TGF-$\beta 3$ on osteoblasts

TGF-$\beta$ like activities are produced by bone cells and large amounts are found in the extracellular bone matrix, indicating an important physiological function of TGF-$\beta$s in this tissue (2). TGF-$\beta$ stimulates cell replication and collagen production in cultured fetal rat bone cells (3, 4, 5) and induces chondrogenesis of embryonic rat mesenchymal cells. In addition, molecules with TGF-$\beta$ like activity are released in vitro after bone resorption and may effect a link between the coupled processes of bone formation and resorption during remodeling.

In this example, we isolated various cell populations from resected bone fragments by sequential collagenase digestions (2, 3) releasing populations enriched for bone forming cells with the biochemical characteristics associated with the osteoblast phenotype, such as type I collagen production, elevated alkaline phosphatase activity and osteocalcin synthesis (FIGS. 12A, 12B and 12C).

Recombinant TGF-$\beta 3$ bound to specific receptors and had a biphasic stimulatory effect of DNA synthesis, enhanced collagen synthesis and decreased alkaline phosphatase activity in osteoblast-enriched cultures after 23 hours of treatment as shown in FIGS. 12A, 12B and 12C. When protein concentration of TGF-$\beta 3$ and TGF-$\beta 1$ were normalized using both the colloidal gold assay from Collaborative Research (Bedford, Mass.) and silver staining on an SDS polyacrylamide gel, TGF-$\beta 3$ was significantly more potent than TGF-$\beta 1$, with an approximate 3-5 fold lower concentration needed for similar half maximal effects in all three of the above-described biological activities. These results show TGF-$\beta 3$ to be a potent stimulator of bone cell growth and function.

EXAMPLE 6

Effects of TGP-β on the Cells of the Central and Peripheral Nervous System

TGF-β3's utility extends to the repair of neurological disorders by accelerating regeneration of peripheral nerves and in promoting regenerative phenomena in the central nervous system. TGF-β1 appears to stimulate the DNA synthesis of short-term Schwann cell (50). In contrast to its effect on short-term Schwann cells, TGF-β1 inhibited DNA synthesis in glial cells and in long term Schwann cells. Utility of TGF-β3 extends to controlling glial proliferation during development and/or regeneration of the peripheral nervous system. Immunohistochemical staining indicates that TGF-β3 is selectively expressed in the mammalian nervous system (51).

EXAMPLE 7

Effects of TGF-β on Muscle Cells

TGF-β1 is a potent modulator of myocyte differentiation. TGF-β1 blocks the onset of differentiation when added to undifferentiated myoblasts and causes differentiation when added to fully differentiated myocytes (53). TGF-β1 inhibits proliferation (53) and DNA synthesis of myocytes. TGF-β3 is involved in the regulation of cardiomyocyte proliferation. TGF-β1 mMA and protein is rapidly lost following myocardial infarction caused by ligation of a coronary artery (53). After the ligation, there is a marked increase in the TGF-β1 mRNA indicating a significant role for TGF-β in response to the injury to the heart. TGF-β2 and TGF-β3 mRNAs were all expressed constitutively in cultured myocytes extracted from embryonic hearts. TGF-β3 is expressed in skeletal and cardiac myocytes (52). Accordingly, this data extends TGF-β3's therapeutic utility to the repair of muscle after cardiac injury. Moreover, antibodies directed against TGF-β3 and the pro region of TGF-β3 may have a similar therapeutic utility in modulating the activity of TGF-β3 in the repair of muscle after cardiac injury.

EXAMPLE 8

Effects of TGF-β3 in Endothelial Cells

TGF-β3 is a potent inhibitor of endothelial cells. Endothelial cell growth is implicated in the control of neovascularization and plaque formation in atherosclerosis. Accordingly, this data extends the utility of TGF-β3 on modulating dysfunctions involving endothelial cell proliferation including atherosclerosis.

EXAMPLE 9

Evaluation of TGF-β3 for Immunosuppressive Activity In Vitro

Lymphocytes were separated from whole blood using Ficoll-Paque (Pharmacia LKB Biotechnology Inc.). Separated lymphocytes were cultured in T25 flasks in RPMI media containing 10% FCS and IL2 (Lymphocult-Biotest Diagnostics). The cells were maintained in this media to grow out the T-lymphocytes. Actively growing T-cells ($2.2 \times 10^5$ cells/ml) in 10 ml of media were placed in T25 flasks with and without 8 ng/ml TGF-β3. Cell growth was determined by microscopic examination at 40 x magnification and quantitation using a Coulter counter. After 5 days, it was observed that untreated T cells formed a large number of aggregates ($\sim$16 in a field of 0.2 cm$^2$), presumably as single cell divide multiple times without separating. Coulter counter quantitation showed $4.15 \times 10^5$ cells/ml. Cells treated with TGF-β3 at 8 ng/ml formed very few small aggregates and were $3.2 \times 10^5$ cells/ml. TGF-β3 inhibited the proliferation of fresh human T cells showing that it is immunosuppressive. The effects of TGF-β3 on cells mediating immune and inflammatory responses indicates TGF-β3's utility in controlling disorder such as immune dysfunction, inflammation, and septic shock.

EXAMPLE 10

Use of TGF-β3 as a Chemoprotection Agent

The rationale for these experiments is to define conditions which allow for use of TGF-β3 in vivo to protect the immune system during chemotherapy thus preventing infection and additionally allowing use of higher doses of chemotherapy in treatment.

Chemoprotection in vitro

Primary human bone marrow and peripheral blood samples are evaluated for the growth of the different hematopoietic lineages in the presence and absence of exogenous TGF-β3. Stem cell cultures are purged of mature, well differentiated cells. Specifically, buffy coat cells is collected by centrifugation (800 rpm, 10', 5° C.), suspended in McCoy's medium including 10% heat inactivated FCS ('complete medium'). Platelets are removed by Percoll gradient centrifugation (1.050 g/ml; Pharmacia) and a low density, small primitive cell population obtained after re-centrifugation on a Percoll gradient (1.075 g/ml). Individual populations of B- and T-lymphocytes, granulocytes, monocytes and more differentiated erythroid populations can be immunodepleted (5) by panning $2 \times 10^8$ light-density cells with monoclonal antibodies (anti-B1, anti-B4, anti-LyT3, anti-My4, anti-MY8, anti-903, anti-N901, anti-Leu1 and anti-glycophorin A (R10) and WEM-G11) directed against mature cell surface epitopes for 30 minutes on ice. Cells are washed twice in cold complete medium and assayed for progenitor cells (48, 49). The primitive stem cell population are grown in methylcellulose support (Iscove's modified Dulbecco's medium (IMDM; Gibco), 24% FCS, 0.8% dialyzed bovine serum albumin, 100 μM β-mercaptoethanol, and 1.3% methylcellulose in 35 mm Lux culture plates) in the presence of 10 pM, 100 pM and 1000 pM TGF-β3 with and without Mo T-lymphocyte conditioned media, a source of colony stimulating factors (44) in quadruplicate cultures maintained in 5% CO$_2$.

Colony forming units of the various hematopoietic lineages are counted microscopically at 3, 7, 14 and 21 days. An example of this experiment is shown in FIG. 13. Individual colonies may be aspirated onto glass slides, selectively stained with May-Grunewald-Giemsa and the presence of neutrophils, monocytes or eosinophils observed. These experiments allow one skilled in the art to determine if the growth inhibitory action of TGF-β3 is lineage-specific at given doses of TGF-β3, determine the time course of inhibition and determine the dose of TGF-β3 required for inhibition of a given cell type.

As a general rule, the smaller hematopoietic precursors represent more primitive progenitor stem cells while the larger cells are usually more mature, as analyzed by the appearance of maturation-specific cell surface epitopes. Enriched progenitor populations obtained by immuno-depletion as described may be size selected by Percoll gradient centrifugation and different size cell populations evaluated for specific lineages in combinations of Mo conditioned media and TGF-$\beta$3 at 3, 7, 14 and 21 days. Assays for early stem cell populations (HPP-CFU of CFU-A), progenitor cells (CFU-E, CFU-GEMM, BFU-E, CFU-MK), pre-B colony, B colony, T colony, cytolytic T cell, and antigen stimulation assays are currently well developed.

Colonic epithelium

The growth inhibitory effects of TGF-$\beta$3 on primary normal and neoplastic colon organ cultures may be evaluated with a view to establishing TGF-$\beta$3 as a chemoprotective agent to reduce gastrointestinal toxicity in the treatment of patients with chemotherapeutic drugs.

Proliferation of colon cell in various stages of differentiation is measured by [$^3$H]-thymidine incorporation into colon biopsy organ cultures followed by sectioning and staining of the intact crypt. A 1 mm biopsy specimen is gently washed in DMEM, 10% FCS, 37° C. Three micron sections are cut to avoid unequal distribution of radiolabel. Preincubation with TGF-$\beta$3 at 10 pM, 100 pM, and 1 nM is carried out over several time points.

Colon specimens are labeled in 2 ml of DMEM+10%, 37° C. equilibrated in a 5% $CO_2$ incubator, containing 1$\mu$Ci/ml [$^3$H]-thymidine (20 Ci/mmole) for 1 hours. Sections are washed, fixed in 10% formalin, embedded and cut longitudinally to expose the morphology of the colon crypt. Tissue sections are coated with liquid emulsion and autoradiographed.

The proliferation index of cells in various stages of crypt development is determined by microscopic counting of exposed silver grains. Routinely, cells with >4 grains score as positive. In normal tissue, only the lower third of the crypt (containing the stem cell population) are labeled. Adjacent tissue serves as an internal control. The appearance of differentiation markers on colon crypt cells are monitored using available monoclonal antibodies to cytokeritins and colon specific antigen (fetal).

To establish in vitro models for the chemoprotective effects of TGF-$\beta$3, doses of cytotoxic drug in organ culture or in dispersed mixed cell culture required for toxicity are assessed. Organ cultures are prepared as previously described (45). Parallel cultures are incubated in a range of 5-FU concentrations and proliferation measured by [$^3$H]-thymidine incorporation and sectional autoradiography. To establish dispersed, mixed cell colon cultures, biopsy material are cut to >0.5 cm$^2$, washed in phosphate buffered saline (PBS), finely titrated, centrifuged, rinsed, washed (5X) and cultured in a mixture of Leibowitz's medium L15 and suspension modified MEM (SMEM) with a final $Ca^{+2}$ concentration of 0.5 mm, 10% fetal calf serum, 100 units penicillin, 50 $\mu$g/ml streptomycin, 25 $\mu$g/ml gentamicin, 2 mM glutamine, 1 ng/ml epidermal growth factor (EGF), 20 $\mu$g/ml insulin, 10 $\mu$g/ml transferrin, 25 nM sodium selenite and grown on collagen (Type I) coated culture plates (46, 47).

Colon cells grown on collagen coated coverslips in a range of 5-FU concentrations are incubated in [$^3$H]-thymidine (0.2 $\mu$Ci/ml) for thirty minutes, washed and chased overnight in fresh media. Cells are washed, fixed/stained, coverslips dipped in liquid photographic emulsion and autoradiographed. Proliferation is measured by counting exposed silver grains.

Chemoprotection by TGF-$\beta$3 in vitro is measured by pre-addition of a range of TGF-$\beta$3 doses to colon organ or cell cultures followed by 5-FU at or near the toxic dose, and [$^3$H]-thymidine labelling at intervals after exposure to cytotoxic drug as a measure of cellular recovery. TGF-$\beta$3 acting as a chemoprotectant would inhibit the high proliferative growth rate of the normal bone marrow and the intestinal crypt cells. Therefore, TGF-$\beta$3 would decrease the life-threatening side effects of conventional chemotherapy and allows the use of more aggressive dose regimens and maintain colonic integrity and prevent infection.

Chemoprotection in vitro

In order to evaluate TGF-$\beta$3 as a chemoprotective agent in vitro the following experiment was performed.

Mink cells were seeded in 96-well plates at $10^3$ cells/well in 100 $\mu$l of DMEM supplemented with 10% fetal bovine serum. Wells containing treated cells received 25 $\mu$l of TGF-$\beta$3 (50 ng/ml). After 24 hours incubation with TGF-$\beta$3, 25 $\mu$l of colchicine or vinblastine was added. After another 24 hours, the media was removed and the cells washed once with Dulbeccol's PBS and fresh complete media added. The cells were incubated for another 7 days.

Cell growth was quantitated by uptake of 5-[$^{125}$I]iodo-2'deoxyuridine ($^{125}$IUdR) indicating the amount of cell growth as previously described. As seen in FIGS. 14A and 14B, cells preincubated with TGF-$\beta$3 prior to incubation with various doses of chemotherapeutic drugs (i.e. vinblastine and colchicine) showed significantly more uptake of $^{125}$UIdR relative to cells which were incubated with the chemotherapeutic drugs without TGF-$\beta$3. Therefore, cells preincubated with TGF-$\beta$3 were protected from the toxic effects of the chemotherapeutic drugs. Similar results were observed when adriamycin was used as the chemotherapeutics drug. This chemoprotective effect should also be possible with other chemotherapeutic drugs including, but not limited to, 5-fluorouracil, and etoposide.

For TGF-$\beta$3 to be an effective chemoprotectant, it is apparent that the growth of the tumor must be less inhibited than that of normal tissues. This may be achieved either because the tumor is innately resistant to the growth inhibitory effects of TGF-$\beta$3 or via the pharmacokinetics allowing a differential effect in vivo.

The following experiments detail steps used to demonstrate efficacy of TGF-$\beta$3 for chemoprotection in vivo.

Acute Toxicology and Chemoprotection of Normal Mice

Acute administration of escalating doses of TGF-$\beta$3 can be investigated for toxicity (survival, weight loss) in normal Balb/c mice. Various hematologic parameters, progenitor cell assays and immune function assays are undertaken.

The status of the hematopoietic stem cell compartment (total numbers in marrow, spleen and circulation, and cell cycle status) is determined using the in vivo CFU-S assay, and the in vitro CFU-GEMM and high proliferative potential (HPP) CFU assays. Progenitor cells for the erythroid (BFU-E, CFU-E), myeloid (CFU-GM, CFU-M, CFU-G) and megakaryocyte/platelet series (CFU-MK) are assayed. Lymphoid function is measured by B- and pre B-lymphocyte colony assays, etc. Subsets of myeloid and lymphoid cells in tissues is determined by FACS analysis using lineage-specific MAbs. WBC, platelets, red blood count (RBC) and hematocrit are measured in repeated tail vein blood samples. Serum samples are obtained and are assayed for TGF-β, G-CSF, GM-CSF, M-CSF, IL-1,3,4,5 and TNF by bioassay and radioimmunoassay. Neutrophil function assays include in vivo and in vitro chemotaxis, bactericidal capacity and receptor expression for multiple cytokines.

The ability of TGF-β3 to protect hematopoietic stem cells from the cytotoxic effects of chemotherapeutic agents is assessed in animal models. Untreated BALB/C mice, or groups pretreated with TGF-β3, receive a single i.v. dose of 5-FU (150 mg/kg). In subsequent experiments cyclophosphamide (200 mg/kg), vinblastine (2.5 mg/kg), adriamycin (2.5 mg/kg) or methotrexate (150 mg/kg) is employed. The number of peripheral circulating blood cells and the various hematopoietic progenitor cells are determined, including CFU-S, CFU-GM, HPP-CFU-C, BFU-E, CFU-MK and CFU-GEMM.

Experiments include altering the dose of TGF-β3 (0.1, 0.5, 2.0, 5.0 and 10.0 μg/animal) as well as the time course of TGF-β3 administration with respect to chemotherapy (48 h, 24 h or 12 h before chemotherapy).

Pharmacokinetics of TGF-β3

The chemical half-life of TGF-β3 is determined in the serum of mice following bolus injections (0.1-10 μg/mouse) via i.v., i.p., and s.c. routes, using internally labelled TGF-β3 (labelled metabolically with $^{35}$S cysteine) or $^{125}$I TGF-β3. Tissue distribution of labelled material is measured in various organs with particular emphasis on liver, spleen and bone marrow sites. If the biological half-life of TGF-β3 in vivo is found to be unacceptably short regional administration by direct intrasplenic injection (through the body wall) is employed or using the surgical technique reported by Goey et al (7) involving injection into the femoral artery. This latter approach has been reported to be effective in localizing TGF-β1 to the marrow with resulting inhibition of early stem cell and progenitor cell proliferation.

Chemotherapy and TGF-β3 in a Spontaneous Breast Tumor Model

The translation of preclinical laboratory results to clinical cancer therapy depends to a very large extent on the relevance of the laboratory model employed. Because of the obvious shortcomings of the long transplanted reurine tumor models and the xenograft human tumor models in nude mice, it is preferable to select the CDF1 breast tumor model. CDF1 shows a remarkable 100% correlation in chemotherapeutic sensitivity to drugs which are considered to be active against human breast cancer.

It is preferable, although not necessary, to identify the optimal parameters of dosage and scheduling relationships by the experiments hereinabove, i.e. TGF-β3 is tested in this model. Most of the planned studies are performed using first generation syngeneic transplants of spontaneous breast tumors. In addition to determination of life span, the effect of therapy is determined on tumor growth rate, on partial and complete regression, and on spontaneous metastasis (determined histologically or by tissue retransplantation). TGF-β3 is tested for its ability to mediate a reversible cytostatic block on hematopoietic progenitor and stem cell proliferation, conferring resistance to toxicity of chemotherapy.

These experiments define conditions in which TGF-β3 can act as a chemoprotective agent in vivo. These conditions are used by one skilled in the art to administer to a patient a suitable amount of TGF-β3 prior to cytotoxic chemotherapy.

EXAMPLE 11

Use of TGF-β3 in Autologous Bone Marrow Transplantation

Autologous bone marrow transplantation is a method in which the bone marrow of a patient is removed prior to chemotherapy to reduce hematopoietic stem cell toxicity. Autologous bone marrow transplantation has also been performed in patients with acute nonlymphocytic leukemia using 4-hydroperoxycyclophosphamide to treat the marrow ex vivo (21).

In one instance, TGF-β3 is used to inhibit the proliferation of the bone marrow stem cell population prior to chemotherapy of bone marrow in vivo in patients with blood-bone tumor cells. Briefly, TGF-β3 is contacted with the patient bone marrow at a sufficient concentration to inhibit the normal hematopoietic cells (for example, 1-1000 pM) as determined by one skilled in the art. At a given time after TGF-β3 treatment of bone marrow ex vivo (typically but not limited to 6-24 hours or as determined by the physician) and the tumor cell population refractory to the effects of TGF-β3, the cells are treated with a cytotoxic chemotherapeutic agent (e.g. adriamycin, 5-fluorouracil, and vinblastine). The treated marrow is returned to the patient at a time determined by the physician and the normal hematopoietic cells allowed to recover from the growth inhibiting effects of TGF-β3 and proliferate, thus reconstituting that component of the patients hematopoietic system.

Alternatively, the bone marrow cells are treated with TGF-β3 as described and the bone marrow cells cultured ex vivo as described (118) such that the leukemic cell population continues to proliferate and terminally differentiate while the normal population is growth arrested. Continued culture in this way results in the terminal growth arrest of the leukemic population and enrichment of the normal cell population. Further, enrichment of the normal cell population may be accelerated by contacting the normal cell population with hematopoietic growth factors, e.g. GM-CSF and IL-3. Bone marrow thus treated is returned to the patient, substantially free of leukemic cells.

EXAMPLE 12

Expression of a Pro Region of the TGF-β3 Precursor Separated from Mature TGF-β3

The pro region of the TGF-β3 precursor associates with the mature TGF-β3 and modifies the biological activity and half life of mature TGF-β3. Nucleic acid encoding the TGF-β3 precursor beginning with methionine at nucleotide positions 263-265 and ending with arginine at position 1160-1162 is engineered by mutagenesis of the nucleic acid in FIG. 1 to introduce a translation termination codon (TGA, TAG, TAA) at position 1163-1165. The resulting nucleic acid is inserted in an expression vector and transfected into a suitable host cell with an additional selectible marker, as previously described. TGF-β3 pro region protein is recovered from the culture medium. This protein binds mature TGF-β3 and thereby sequesters and modifies the half life and biological activity of the mature TGF-β3.

Binding assay of TGF-β3 to the TGF-β3 pro region protein

The binding of TGF-β3 pro region to TGF-β3 or mutant TGF-β3 is measured by the following. $^{125}$I TGF-β3 is incubated with purified TGF-β3 pro region in PBS with either unlabeled TGF-β3 or mutant TGF-β3 for 5 hr on ice. Non-specific binding is determined using a 400-fold molar excess of unlabeled growth factor. Crosslinking of the TGF-β3 pro region to $^{125}$I TGF-β3 is accomplished with the addition of a ¼ volume of 5 mM bis(sulfosuccinimidyl)suberate (BS$^3$; Pierce) in PBS and the reaction is stopped after 2 min at 4° C. by the addition of 1/20 volume of 2.5M glycine. An equal volume of SDS-PAGE sample buffer (2X) is added to the sample is heated in a boiling water bath for 3 min.

Electrophoresis is performed on the samples and destained gels is dried and exposed at $-70°$ C. to X-ray film using intensifying screens. Alternatively, antI-TGF-β3 is used to immunoprecipitate the TGF-β3 pro region complexed with $^{125}$I TGF-β complex with or without crosslinking and quantitated directly by a gamma counter.

EXAMPLE 13

Inhibition of TGP-β by a TGP-β binding protein

It would be clear to those skilled in the art that TGF-β3 is a bifunctional growth factor. The experiments disclosed herein illustrate that TGF-β3 inhibits or stimulates the same target cell depending upon the exposure time and concentration of other exogenous factors. As a potent modulator of cell growth and differentiation, the regulation of TGF-β3 levels and exposure of target cells to TGF-β3 in concert with these other factors is important for normal tissue function and development.

Specifically herein the pro region of the TGF-β precursor and the antibodies directed against the mature TGF-β can be administered to a patient in a suitable carrier in a pharmaceutically suitable amount to neutralize, or modify clearance of, systemic TGF-β thereby treating the patient suffering from a disorder or symptoms associated with excess TGF-β. Examples of disorders associated with excess TGF-β include, but are not limited, connective tissue disorder (for example fibrosis and scleroderma), immunosuppression, myocardial ischemia, myopathic disorder, certain cancers associated with elevated levels of TGF-β (for example glioblastoma), neurological, inflammatory, AIDS viral infection and atherosclerosis.

Additionally, the pro region of the TGF-β precursor could be used as a vehicle for delivery of mature TGF-β thereby modifying the half life and biological activity of the mature TGF-β.

EXAMPLE 14

Effects of TGF-β3 on Fibroblasts

TGF-β3 enhances cell growth, alone or in combination with other molecules. For example, TGF-β3 may directly affect DNA synthesis. Alternatively, TGF-β3 synergizes with other factors to promote cell growth. Accordingly, when contacted with fibroblasts in vitro or in vivo, TGF-β3 acts to promote connective tissue repair, dermatological repair and wound healing.

REFERENCES

1. Barker, C.R., Worman, C.P., and Smith, J.L (1975) *Immunology* 29:765–777.
2. Centrella, et al. (1988) *FASEB J.*, 2:3066)
3. Centrella, et al. (1988) *Proc. Natl. Acad. Sci.* USA, 85:5889
4. Centrella, et al. (1987) *J. Biol. Chem*, 262:2869;
5. Centrella, et al. (1986) *Endocrinol.* 119:2306)
6. Gentry, L.E. et al. (1987) *Mol. Cell. Biol.* 7:3418–3427.
7. Goey, H. et al.(1989) *J. Immunol.* 143:877–880.
8. Graham, F.L. and van der Eb, A.J. (1973) *Virology* 52:456–457.
9. Harlow, E. and Lane D. (1988) In Antibodies, A Laboratory Manual, Cold Spring Harbor.
10. Iwata, K.K. et al. (1985) *Cancer Res.* 45:2689–2694.
11. Kozak, M. *Cell* (1986) 44:283–292
12. Lowry, (1957) *Methods Enzymol* 4:366–381
13. Madisen, L. et al. (1989) *DNA* 8:205–212.
14. McCarthy, et al. (1988) *J. Bone Min. Res.* 3:401
15. Nakamaye, K. and Eckstein, F. (1986) *Nucleic Acids Res.* 14:9679–9698.
16. Perlman and Halvorson (1983) *J. Mol. Biol.* 107:391–409.
17. Seyedin, et al. (1986) *J. Biol. Chem.* 261:5693.
18. Tashjian, et al. (1985) *Proc. Natl. Acad. Sci.* USA, 82:4535.
19. Urlaub, G. and Chasin, A. (1980) *Proc. Natl. Acad. Sci.* USA 77:4216–4220.
20. Wong, et al (1975) *Proc. Natl. Sci.* USA 72:3167–3171.
21. Cashman, J.D. et al. (1990) *Blood*, 75:96.
22. Mossman, T. (1983) *J. Immuno. Methods* 65:55–65.
23. Massague (1987) *Cell* 49(4):437.
24. Brunner et al. (1988) *Mol. Cell. Biol.* 8(5):2229.
28. Madisen et al. (1988) *J. Cell Biochem. Suppl.* pp 199.
29. Pincher et al. (1985) *Biochem. Biophys Res Commun.*, 133 (3):1026.
30. Derynck et al. (1986) *J. Biol. Chem.* 261(10):4377
31. Twardzik et al. (1989), *J. Natl. Cancer Inst.* 81(15):1182.
32. D. A. Lawrence et al. (1985) *Biochem. Biophys. Res. Commun.* 133(3):1042.
33. J. Keski-Ohta et al. (1986) *J. Cell. Biol.* 103:445.
34. L.R. Ellingsworth et al. (1986) *J. Biol. Chem.* 261(26):12362.
35. J. Keski-Oha et al. (1987) *Cancer Res.* 47(24):6451.
36. K. Flanders et al. (1987) *J. Cell. Biochem Suppl.* pp. 58.
37. Morrison, S.L. (1984) *Proc. Natl. Acad. Sci. U.S.A.*, 84:6851.
38. Morrison, S.L. et al. (1987) *Ann. N.Y. Acad. Sci.* 507:187.
39. Morrison, S.L. et al. (1988) *Clin. Chem.* 34:1668.
40. Neuberger, et al. (1984) *Nature* (London), 312:604.
41. Neuberger, M.J. et al. (1985) *Nature* (London), 314:268–270.
42. Oi, V.T., et al. (1984) *Nature* 307:136–140.
43. Oi, V.T., and Morrison, S.L. (1986) *BioTechnigues* 4:214.
44. Golde, D.W. et al. (1980) *Proc. Natl. Acad. Sci.* USA 77, 593–597.
45. Shamsuddin, A.M. (1990) In: Colon Cancer Cells., M. Moyer and G. Poste, pp 137–153, Academic Press, New York.
46. Wong, et al (1975) *Proc. Natl. Acad. Sci.*, USA 72:3167–3171

47. Moyer, M et al. (1990) In 'Colon Cancer Cells'Ed. M. Moyer and G. Poste, pp. 85-136, Academic Press, New York.
48. Strife, A. et al. (1988). *Cancer Res.* 48, 1035-1041.
49. Strife, A. (1987) *Blood* 69:1508-1523.
50. Davis, J. B. and Stroobert, P, (1990) *J. Cell Bio.*, 110: 1353.
51. Wilcox, J. N. and Derynck, R. (1988) *J. Neuroscience*, 8:1901.
52. Thompson, N. L., et al., (1988) *Growth Factor*, 1:91-99.
53. Florini, J. R., et al., (1986) *Journ, Biol. Chem.*, 261:16509.
54. Assoian, et al. (1983) *J. Biol. Chem*, 258:7155
55. Wrann, M. et al. (1987) *EMBO J.* 6:1633-1636.

What is claimed is:

1. A method for obtaining bone marrow essentially free of actively dividing tumor cells which comprises:
   (a) contacting for 24 hours bone marrow containing hematopoietic cells and actively growing tumor cells with a concentration of a TGF-$\beta$3 at 1000 pM such that the growth of the normal hematopoietic cells is temporarily inhibited;
   (b) after 24 hours contacting bone marrow with a tumor inhibiting drug so that growth of the tumor cells is permanently prevented; and
   (c) culturing bone marrow so as to permit growth of normal hematopoietic cells thereby obtaining bone marrow essentially free of actively dividing tumor cells.

* * * * *